US008885909B2

(12) United States Patent
Takagi

(10) Patent No.: US 8,885,909 B2
(45) Date of Patent: Nov. 11, 2014

(54) RADIOGRAPHIC-IMAGE PROCESSING APPARATUS

(75) Inventor: Tatsuya Takagi, Musashino (JP)

(73) Assignee: Konica Minolta Medical & Graphic, Inc., Tokyo (JP)

(*) Notice: Subject to any disclaimer, the term of this patent is extended or adjusted under 35 U.S.C. 154(b) by 157 days.

(21) Appl. No.: 13/698,424

(22) PCT Filed: Feb. 25, 2011

(86) PCT No.: PCT/JP2011/054280
§ 371 (c)(1),
(2), (4) Date: Nov. 16, 2012

(87) PCT Pub. No.: WO2011/145377
PCT Pub. Date: Nov. 24, 2011

(65) Prior Publication Data
US 2013/0071000 A1    Mar. 21, 2013

(30) Foreign Application Priority Data

May 17, 2010    (JP) ................................ 2010-112739

(51) Int. Cl.
| | | |
|---|---|---|
| G06K 9/00 | (2006.01) |
| A61B 6/00 | (2006.01) |
| G06T 5/20 | (2006.01) |
| H04N 5/365 | (2011.01) |
| G06T 5/00 | (2006.01) |
| H04N 1/409 | (2006.01) |

(52) U.S. Cl.
CPC ............ *A61B 6/5258* (2013.01); *A61B 6/4233* (2013.01); *A61B 6/4283* (2013.01); *A61B 6/5252* (2013.01); *A61B 6/4405* (2013.01); *G06T 5/20* (2013.01); *H04N 1/409* (2013.01); *H04N 5/3656* (2013.01); *H04N 5/3658* (2013.01); *G06T 5/002* (2013.01); *G06T 2207/10116* (2013.01); *G06T 2207/20012* (2013.01); *G06T 2207/20192* (2013.01); *G60T 2207/20224* (2013.01)
USPC ........................................................ 382/132

(58) Field of Classification Search
None
See application file for complete search history.

(56) References Cited

U.S. PATENT DOCUMENTS 5,065,444 A    11/1991    Garber
5,717,791 A *   2/1998    Labaere et al. ............... 382/274
(Continued)

FOREIGN PATENT DOCUMENTS

FR          2686471 A1    7/1993
JP          06-342099 A   12/1994
(Continued)

OTHER PUBLICATIONS

International Search Report dated May 17, 2011 (in English) in counterpart International Application No. PCT/JP2011/054280.

(Continued)

*Primary Examiner* — Shervin Nakhjavan
(74) *Attorney, Agent, or Firm* — Holtz, Holtz, Goodman & Chick PC

(57) ABSTRACT

A radiographic-image processing apparatus that can accurately remove striated artifacts superimposed onto image data taken by an FPD radiographic imaging device includes: a partitioning section that partitions a region, in which image data taken by a radiographic imaging device is arranged two-dimensionally, into segments; a mean-value computation section that computes mean values from the image data along the same scanning line in each segment; an edge compression section that compresses mean-value differentials in boundary regions between the imaged subject and the surroundings thereof; a filtering section that applies an adaptive filter to the differential-compressed profile; and a correction-data creation section that creates correction data on the basis of each datum in the adaptive-filtered profile. Image data in which noise is removed is generated by subtracting corresponding correction data from the image data.

9 Claims, 29 Drawing Sheets

(56) References Cited

U.S. PATENT DOCUMENTS

| | | | |
|---|---|---|---|
| 5,832,055 A * | 11/1998 | Dewaele | 378/62 |
| 7,221,782 B1 * | 5/2007 | Kump | 382/128 |
| 2007/0014468 A1 * | 1/2007 | Gines et al. | 382/154 |
| 2008/0056445 A1 * | 3/2008 | Spahn | 378/62 |
| 2010/0316273 A1 * | 12/2010 | Inoue et al. | 382/128 |

FOREIGN PATENT DOCUMENTS

| | | |
|---|---|---|
| JP | 7-72256 A | 3/1995 |
| JP | 09-073144 A | 3/1997 |
| JP | 10-276330 A | 10/1998 |
| JP | 2001-99944 A | 4/2001 |
| JP | 2003-87656 A | 3/2003 |
| JP | 2005-3578 A | 1/2005 |
| JP | 2005-129709 A | 5/2005 |
| JP | 2005-303448 A | 10/2005 |
| JP | 2006-058124 A | 3/2006 |
| JP | 3890163 B2 | 12/2006 |

OTHER PUBLICATIONS

International Preliminary Report on Patentability (IPRP) and Written Opinion dated Dec. 10, 2012 (in English) issued in parent International Application No. PCT/JP2011/054280.

Extended European Search Report (EESR) dated Nov. 11, 2013 (in English) issued in counterpart European Application No. 11783314.5.

* cited by examiner

FIG.11

RADIOGRAPHIC-IMAGE PROCESSING APPARATUS

This application is a U.S. National Phase Application under 35 USC 371 of International Application PCT/JP2011/054280 filed Feb. 25, 2011.

TECHNICAL FIELD

The present invention relates to a radiographic image processing apparatus, and more particularly to an image processing apparatus which removes streaky unevenness from a radiographic image captured with a radiographic image capturing apparatus.

BACKGROUND ART

Radiographic images captured by using radiation, represented by X-ray images, are widely used for the purpose of disease diagnosis and the like. These radiographic images for medical use are conventionally captured by using screen films. However, there has been developed a CR (Computed Radiography) apparatus which uses a stimulable phosphor sheet for digitalizing a radiographic image, and recently, there has been developed a radiographic image capturing apparatus which detects emitted radiation with radiation detection elements such as photodiodes (photoelectric conversion elements) to obtain the emitted radiation as digital image data.

Such type of radiographic image capturing apparatus is know as FPD (Flat panel Detector) and it has been conventionally developed as a so-called specialized machine which is formed integrally with a supporting platform or the like (for example, see patent documents 1 and 2). Further, in recent years, there has developed a portable radiographic image capturing apparatus in which radiation detection elements and the like are housed in a housing so as to be able to carry around and such portable radiographic image capturing apparatus has been utilized (for example, see patent documents 3 and 4).

As for radiographic image capturing apparatus, there is known a so-called direct type radiographic image capturing apparatus which generates electric charges with detection elements according to radiation doses such as emitted X-rays or the like and converts the electric charges into electric signals and a so-called indirect type radiographic image capturing apparatus which converts emitted radiation into electromagnetic waves of other wave length such as visible light or the like by a scintillator or the like and thereafter generates electric charges with photoelectric conversion elements such as photodiodes according to energy of the electromagnetic waves which are converted and emitted and converts the generated electric charges into electric signals. Here, in the present invention, detection elements in such direct type radiographic image capturing apparatus and photoelectric conversion elements in such indirect type radiographic image capturing apparatus are called radiation detection elements all together.

In patent documents 5 and 6, there are suggested radiographic image processing apparatuses and the like for generating radiographic images without unevenness by removing unevenness that occurs in radiographic images from radiographic images obtained with a conventional CR apparatus. In such radiographic image processing apparatuses and the like, by extracting unevenness components from a captured radiographic image and removing the extracted unevenness components from the original radiographic image, a radiographic image without unevenness can be generated.

In case of a CR apparatus, radiographic image capturing is carried out by emitting radiation onto a plate or the like including a stimulable phosphor sheet layer via a subject and the plate or the like is conveyed to a radiographic image reading apparatus so that a radiographic image is to be read out from the plate in the radiographic image reading apparatus.

At that time, as shown in FIG. 26, a laser beam output from a laser diode 101 is made to be parallel light by a collimator lens 102, a part of the parallel light reflects off a beam splitter 103 to be sent to a detector 104 and the monitoring result by the detector 104 is fed back to a laser drive circuit 105 so that the laser output from the laser diode 101 is adjusted in the radiographic image reading apparatus 100, for example.

Further, most part of the parallel light is refracted by an imaging lens 106 formed of a cylindrical lens and reflects off the mirror surface of a polygon mirror 107 and the reflection light is emitted onto the image surface of the plate P via a fθ lens 108 and a cylindrical mirror 109. At that time, by the polygon mirror 109 rotating, the laser beam which enters the image surface of the plate P travels in the main scanning direction X on the image surface as an excitation light and scans the image surface along the reading line Z.

When the laser beam which is excitation light enters the image surface of the plate P, radiation energy accumulated at a position in the stimulable phosphor layer of the plate P where laser beam enters is emitted as fluorescence. Then, the emitted fluorescence goes through a light-guiding tube 110a of a light concentrating device 110 to be concentrated at the light concentrating device 110 and the concentrated fluorescence is guided to a photomultiplier or a photodiode 111. The photodiode 111 or the like responds to the concentrated fluorescence and outputs output current.

In such way, pieces of image data of individual pixels on the plate P are obtained. Here, sub-scanning direction Y is the direction orthogonal to the main scanning direction X, and the plate P is subjected to scanning by the laser beam which is excitation light as described above while gradually moving in the sub-scanning direction Y. Thereby, pieces of image data of individual pixels on the plate P are read in two dimensional manner, and image data is read.

For example, in the radiographic image processing apparatus described in patent document 6, the pieces of read image data are arranged in two dimensional manner and the pieces of read image data are divided in strip-shaped areas Sa extending in the sub-scanning direction Y, for example, to obtain image data distribution of pixels aligned in the sub-scanning direction Y for each strip-shaped region Sa as shown in FIG. 27. Further, there is suggested to generate a radiographic image p without unevenness by performing high-pass filter processing or low-pass filter processing on the image data distribution to extract unevenness components in the original radiographic image p and remove the extracted unevenness components from the original radiographic image p.

Unevenness that occurs in the radiographic image p captured with a CR apparatus mainly occurs due to physical vibration of each member of the radiographic image reading apparatus 100, such as the polygon mirror 107 of the radiographic image reading apparatus 100 vibrating when it rotates and the cylindrical mirror 109 vibrating.

In view of the above, when the invention described in patent document 6 is to be applied, each member of the radiographic image reading apparatus 100 is adjusted so that cycles of vibration of each member occurs in a high-frequency side, for example, in most cases. By configuring the radiographic image reading apparatus 100 as described above, cycles of unevenness components that occur in a radiographic image p can be in the high-frequency side, for example.

Further, in image data where internal organs, bones and the like of a human body are captured, image data distribution appears more in a low-frequency side (that is, in long cycle side). Therefore, by performing high-pass filter processing, for example, on the image data distribution, unevenness components remain and image data components where internal organs, bones and the like of a human body are captured are cut off. Thus, in such case, only the unevenness components can be extracted from the radiographic image p by the high-pass filter processing.

PRIOR ART DOCUMENTS

Patent Documents

Patent document 1: Japanese Patent No. 3890163
Patent document 2: Japanese Patent Application Laid-Open Publication No. H9-73144
Patent document 3: Japanese Patent Application Laid-Open Publication No. 2006-058124
Patent document 4: Japanese Patent Application Laid-Open Publication No. H6-342099
Patent document 5: Japanese Patent Application Laid-Open Publication No. H10-276330
Patent document 6: Japanese Patent Application Laid-Open Publication No. 2005-303448

DISCLOSURE OF THE INVENTION

Problem to be Solved by the Invention

However, when radiographic image capturing is to be carried out with the above described FPD type radiographic image capturing apparatus, practically speaking, it is difficult to configure so that vibration cycles of each of devices and members constituting the radiographic image capturing apparatus occur in high-frequency side, for example, by adjusting each of the devices and members.

Further, it is known that unevenness occurs in captured radiographic images P due to a reason other than the reason in the above case of radiographic image reading apparatus in radiographic image capturing apparatus.

That is, in radiographic image capturing apparatus, as shown in FIGS. 5 and 7 for example, a plurality of scanning lines 5 and a plurality of signal lines 6 are provided on a substrate 4 so as to intersect each other and a plurality of radiation detection elements 7 are two dimensionally arranged by being set in sections r defined by the scanning lines 5 and the signal lines 6, individual radiation detection elements 7 being arranged respectively in the sections r.

Then, after radiation image capturing is carried out by a radiographic image capturing apparatus being irradiated by radiation via a subject, ON voltage is sequentially applied to the lines L1 to Lx which are scanning lines 5 from a gate driver 15b of a scanning drive unit 15 as shown in FIG. 28, for example, and pieces of image data are sequentially read out from the individual radiation detection elements 7 by the electric charges accumulated in the individual radiation detection elements 7 due to radiation irradiation being read out by a reading circuit 17 via each signal line 6.

At this time, noise occurs in the voltage which is to be applied to each scanning line 5 and each bias line 9 at a power supply 15a of the scanning drive unit 15 and a bias power supply 14 (see FIG. 7). Then, the noise that occurs in the power supply 15a and the bias power supply 14 is superimposed as charge noise on each electric charge read out from each radiation detection element 7 connected to a line Ln of the scanning lines 5 by ON voltage being applied to the line Ln which is scanning line 5 at the moment when the read-out processing is performed.

Therefore, the same charge noise is superimposed on each of the electric charges read out from the radiation detection elements 7 connected to the line Ln of the scanning lines 5. Further, the same charge noise is similarly superimposed on each of the electric charges read out from the radiation detection elements 7 connected to the line Ln+1 of the scanning lines 5 by On voltage being applied to the line Ln+1 which the next line in the scanning lines 5.

In such way, the same charge noise is superimposed on each of pieces of image data d read out from the radiation detection elements 7 with respect to the radiation detection elements 7 which are connected to the same line L of the scanning lines 5. However, as shown in FIG. 28, ON voltage is applied to the lines L1 to Lx of scanning lines 5 at different timings and the size of noise that occurs in the power supply 15a and the bias power supply 14 differs between the timings.

Therefore, when focusing on the noise component to be superimposed on each piece of image data and not on each piece of image data it self, although the same noise is superimposed with respect to each of the radiation detection elements 7 connected to the same scanning line 5, the size of noise to be superimposed is different among scanning lines 5. Thus, as shown in FIG. 29, streaky unevenness that extends in the extending direction of the scanning lines 5 appears in the radiographic image p.

As described above, when image data is obtained with a FPD type radiographic image capturing apparatus, there is a characteristic that streaky unevenness that extends in the extending direction of scanning lines 5 appears in the radiographic image p which is generated on the basis of the image data. Here, in FIG. 29, the extending direction of scanning lines 5 is indicated by an arrow A and the extending direction of signals lines 6 which are orthogonal to the scanning lines 5 is indicated by an arrow B.

In view of the above, in image processing which is to be performed on image data obtained by a FPD type radiographic image capturing apparatus, it is preferred that such characteristic streaky unevenness is accurately removed.

The present invention was made in view of the above problems, and an object of the present invention is to provide a radiographic image processing apparatus which can accurately remove streaky unevenness which is superimposed on image data captured by a FPD type radiographic image capturing apparatus.

Means for Solving the Problem

In order to solve the above problem, a radiographic image processing apparatus of the present invention is which performs image processing on pieces of image data of radiation detection elements captured by a radiographic image capturing apparatus wherein the radiographic image capturing apparatus comprises a detection unit in which radiology detection elements are arranged in two dimensional manner, the radiology detection elements being provided respectively in sections which are sectioned by a plurality of scanning lines and a plurality of signal lines arranged so as to intersect each other, and the radiographic image processing apparatus includes a dividing unit which divides a region in section areas by sectioning the region, in which the pieces of image data are arranged in two dimensional manner, in units of a predetermined number of pieces of image data at least in an extending direction of the scanning line on the detection unit when the pieces of image data are arranged in two dimensional manner so as to correspond respectively with the plurality of radiation detection elements arranged in two dimensional manner;

an average value calculation unit which performs a calculation of an average value of the pieces of image data aligned in the extending direction of a same scanning line among the pieces of image data in a section area for each of the scanning lines for each of the section areas;

an edge compression unit which generates a profile in which a difference in average values of the pieces of image data which occurs at a border of a captured subject and a surrounding thereof is compressed for each of the section areas with respect to a signal line extending direction profile of the average values of the pieces of image data of individual scanning lines calculated for each of the section areas;

a filter processing unit which performs processing to apply an adaptive filter to the profile in which the differences are compressed for each of the section areas; and a correction data generation unit which generates pieces of correction data arranged in two dimensional manner by reconstructing pieces of data at other positions in the region on the basis of pieces of data in the profiles to which the adaptive file is applied, and pieces of image data in which noises are removed are generated respectively for the radiation detection elements by subtracting the pieces of correction data of corresponding positions from the pieces of image data arranged in two dimensional manner, respectively.

Effect of the Invention

According to the radiographic image processing apparatus of a format according to the present invention, each of processing performed by the dividing unit, processing performed by the average value calculation unit, processing performed by the edge compression unit, processing performed by the filter processing unit and processing performed by the correction data generation unit is performed on the image data captured with a FPD type radiographic image capturing apparatus, and correction data consists only of streaky unevenness components can be generated by accurately extracting only the streaky unevenness (see FIG. 29) components which extends in the extending direction of scanning lines characteristic to FPD type radiographic image capturing apparatus from the image data.

Therefore, by subtracting the corresponding correction data from the image data, the superimposed streaky unevenness can be accurately removed from the image data and image data in which streaky unevenness is removed can be generated accurately. Further, bay generating a radiographic image on the basis of the image data in which streaky unevenness is removed, streaky unevenness can be removed accurately from the radiographic image and radiographic image without streaky unevenness can be generated.

BRIEF DESCRIPTION OF THE DRAWINGS

FIG. 11 This is a diagram for explaining original image data arranged in two dimensional manner, a region thereof, the extending direction of scanning lines and the extending direction of signal lines.

BEST MODE FOR CARRYING OUT THE INVENTION

Figure 1:
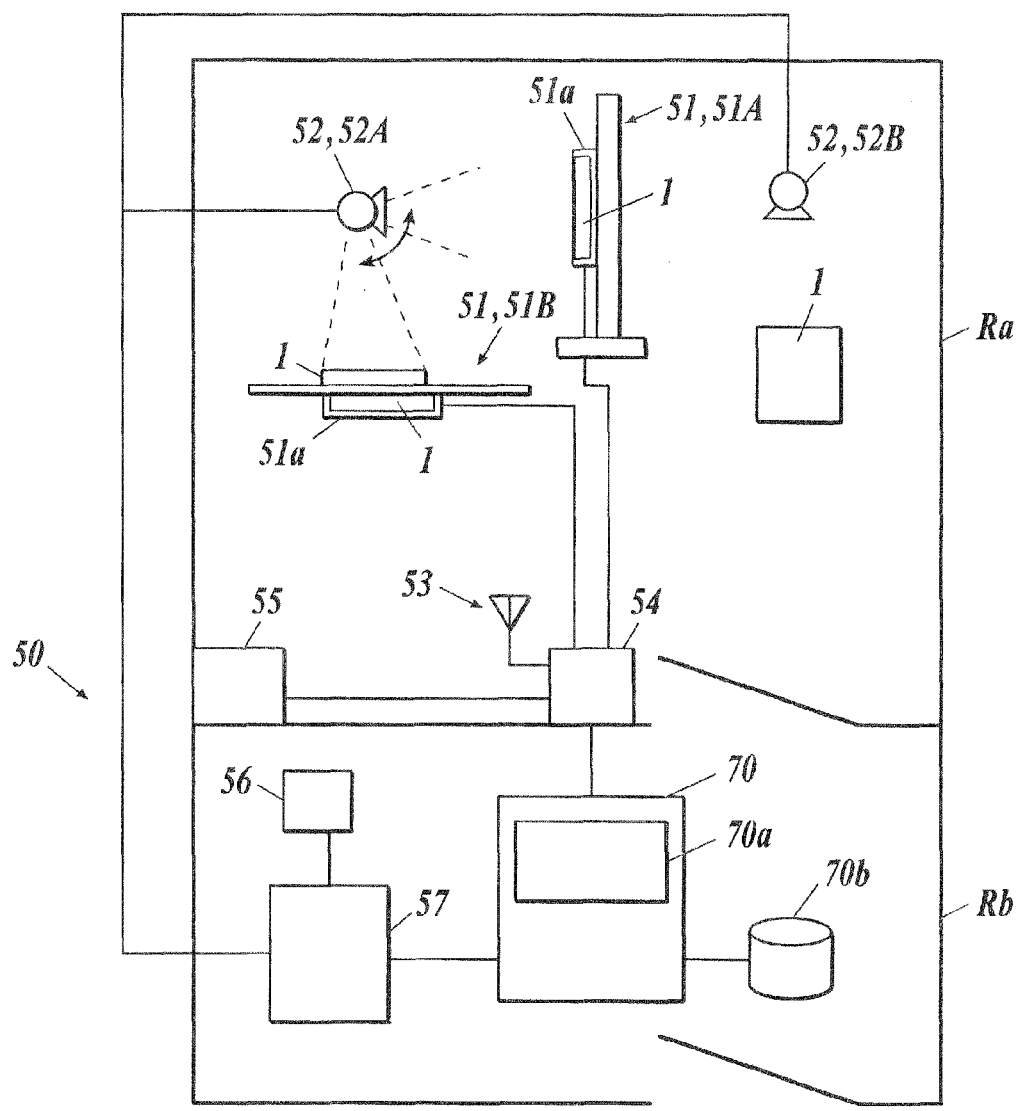
FIG. 1 This is a diagram showing an example of an entire configuration of a radiographic image capturing system for capturing radiographic images which are to be processed by a radiographic image processing apparatus.

Hereinafter, an embodiment of a radiographic image processing apparatus according to the present invention will be described with reference to the drawings. However, the present invention is not limited to the examples shown in the drawings.

Hereinafter, before giving description on a radiographic image processing apparatus, a radiographic image capturing system for capturing a radiographic image which is to be processed by a radiographic image processing apparatus will be described. In the embodiment, it is assumed that the radiographic image capturing system 50 is provided in a hospital, a clinic and the like and it is assumed that a radiographic image capturing apparatus 1 is used to capture the body or the like of a patient.

Here, in the following description, a case where the radiographic image capturing apparatus 1 is a so-called indirect type radiographic image capturing apparatus which includes a scintillator and which converts the emitted radiation into electromagnetic waves having other wavelength such as visible light to obtain electric signals by photoelectric conversion elements will be described. However, the radiographic image capturing apparatus 1 may be a direct type radiographic image capturing apparatus. Further, hereinafter, a case where the radiographic image capturing apparatus is a portable type will be described. However, the radiographic image capturing apparatus may be the type which is integrally formed with a supporting platform or the like.

Moreover, in the following description, a case where the radiographic image processing apparatus 70 is provided in a front room Rb by being associated one to one with the image capturing room Ra and the radiographic image processing apparatus 70 also functions as a computer (so-called console) to control each device in the image capturing room Ra and the like will be described as mentioned later.

However, for example, configuration may be such that the console which controls each device in the image capturing room Ra and the like is provided separately by being associated with the image capturing room Ra, the radiographic image processing apparatus 70 is set at a place other than the image capturing room Ra or the front room Rb and the radiographic image processing apparatus 70 and the console are connected via a network such as LAN (Local Area Network) or the like.

Further, for example, configuration may be such that the radiographic image processing apparatus 70 and a plurality of image capturing rooms Ra are connected via a network or a plurality of radiographic image processing apparatuses 70 and a plurality of image capturing rooms Ra are connected via a network. Furthermore, the radiographic image capturing system 50 can be arbitrarily configured so as to appropriately perform image processing on a radiographic image p by the radiographic image processing apparatus 70.

The image capturing room Ra is a room to carry out radiographic image capturing by emitting radiation onto a subject which is a part of the body of a patient (that is, an image capturing part of a patient), and a radiation source 52 or the like of a radiation generation device 57 of the radiation emitting device for emitting radiation onto a subject and the like are arranged in the image capturing room Ra. Further, in the image capturing room Ra, a bucky 51 in which a radiographic image capturing apparatus 1 is to be loaded is provided.

Figure 2:
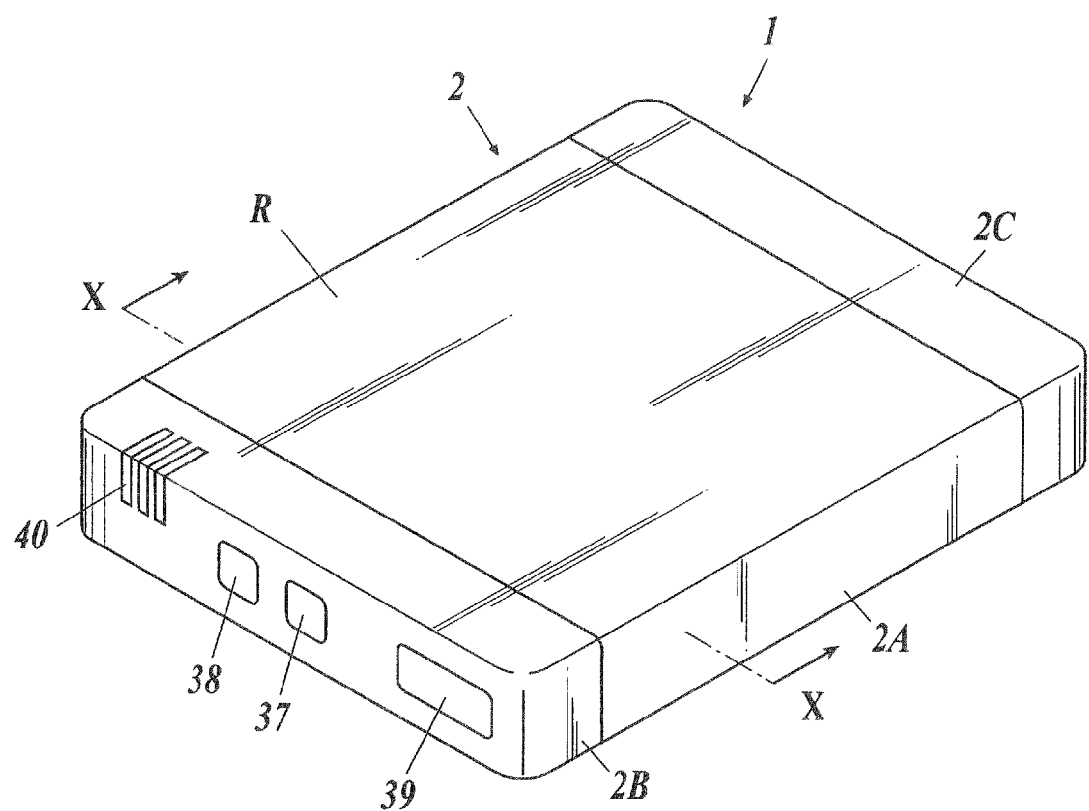
FIG. 2 This is an outer schematic view of the radiographic image capturing apparatus.
Figure 3:
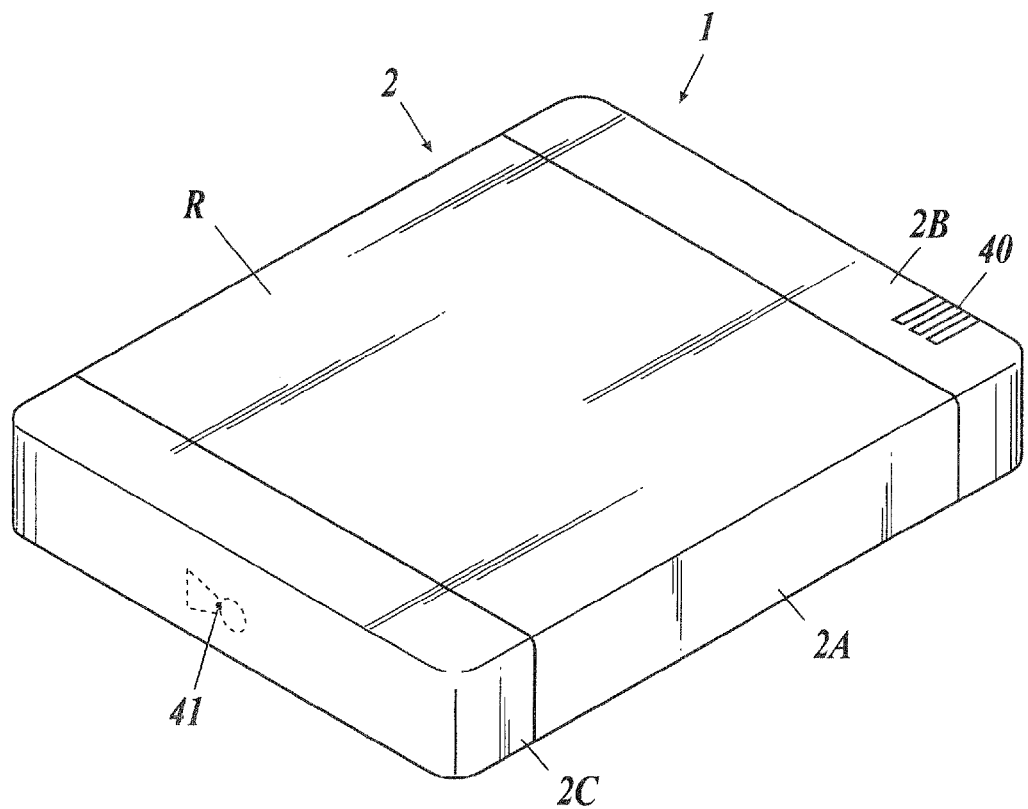
FIG. 3 This is an outer schematic view when the radiographic image capturing apparatus of FIG. 2 is seen from the opposite side.
Figure 4:
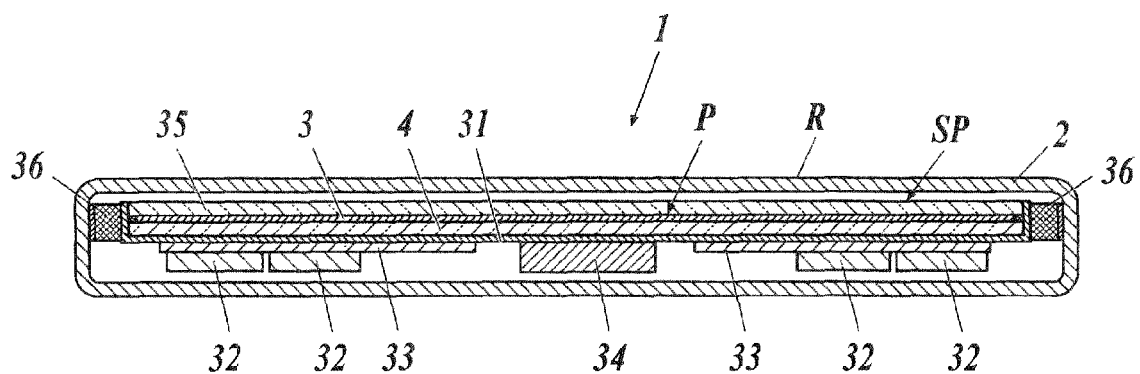
FIG. 4 This is a sectional view when cut along the line X-X in FIG. 2.

Here, the radiographic image capturing apparatus 1 will be described. FIG. 2 is an outer schematic view of the radiographic image capturing apparatus according to the embodiment and FIG. 3 is an outer schematic view when the radiographic image capturing apparatus is seen from the opposite side. Further, FIG. 4 is a sectional view when cut along the line X-X in FIG. 2. As shown in FIGS. 2 to 4, the radiographic image capturing apparatus 1 is configured by housing a sensor panel SP consists of a scintillator 3, a substrate 4 and the like in a case-shaped housing 2.

As shown in FIGS. 2 and 3, in the embodiment, the square tube shaped housing main body 2A of the case 2 which is hollow inside including a radiation entering surface R is formed of material such as a carbon plate or plastic which passes radiation therethrough, and the case 2 is formed by closing the openings in both sides of the housing main body 2A with lid members 2B and 2C. Here, instead of forming the case 2 as a so-called monocoque type, the case 2 may be formed as a so-called lunch box type formed of a frame plate and a back plate, for example.

As shown in FIG. 2, a power switch 37, a selection switch 38, a connector 39 and an indicator 40 which is formed of LED or the like and indicates the battery condition, the activation condition of the radiographic image capturing apparatus 1 and the like are arranged on the lid member 2B in one side of the case housing 2.

Further, as shown in FIG. 3, an antenna device 41 which is a communication unit for sending image data and the like to the radiographic image processing apparatus 70 through wireless transmission is embedded in the lid member 2C in the other side of the case 2. Here, image data and the like may be sent through wired communication to the radiographic image processing apparatus 70, and in such case, sending and receiving is performed by connecting a cable or the like to the above mentioned connector 39, for example. Further, when the antenna device 41 is to be provided, the arrangement position of the antenna device 41 on the case 2 and the number of antenna devices 41 to be disposed are decided arbitrarily.

As shown in FIG. 4, in the case 2, a base 31 is disposed on the lower surface of the substrate 4 of the sensor panel SP and a PCB substrate 33 on which electric components 32 and the like are arranged, a cushion member 34 and the like are attached on the base 31. In the embodiment, a glass substrate 35 for protecting the substrate 4 and the scintillator 3 is provided in the radiation entry face R side of the scintillator 3 and buffers 36 for preventing the sensor panel SP and sides of the case 2 from contacting each other are provide between the sensor panel SP and the sides of the case 2.

The scintillator 3 is adhered on the after-mentioned detection unit P of the substrate 4. In the embodiment, a scintillator which includes phosphor as main component and which converts radiation into electromagnetic waves having wavelength of 300 to 800 nm, that is, electromagnetic waves centered around visible light, when radiation is entered to output the electromagnetic waves is applied as the scintillator 3.

Figure 5:
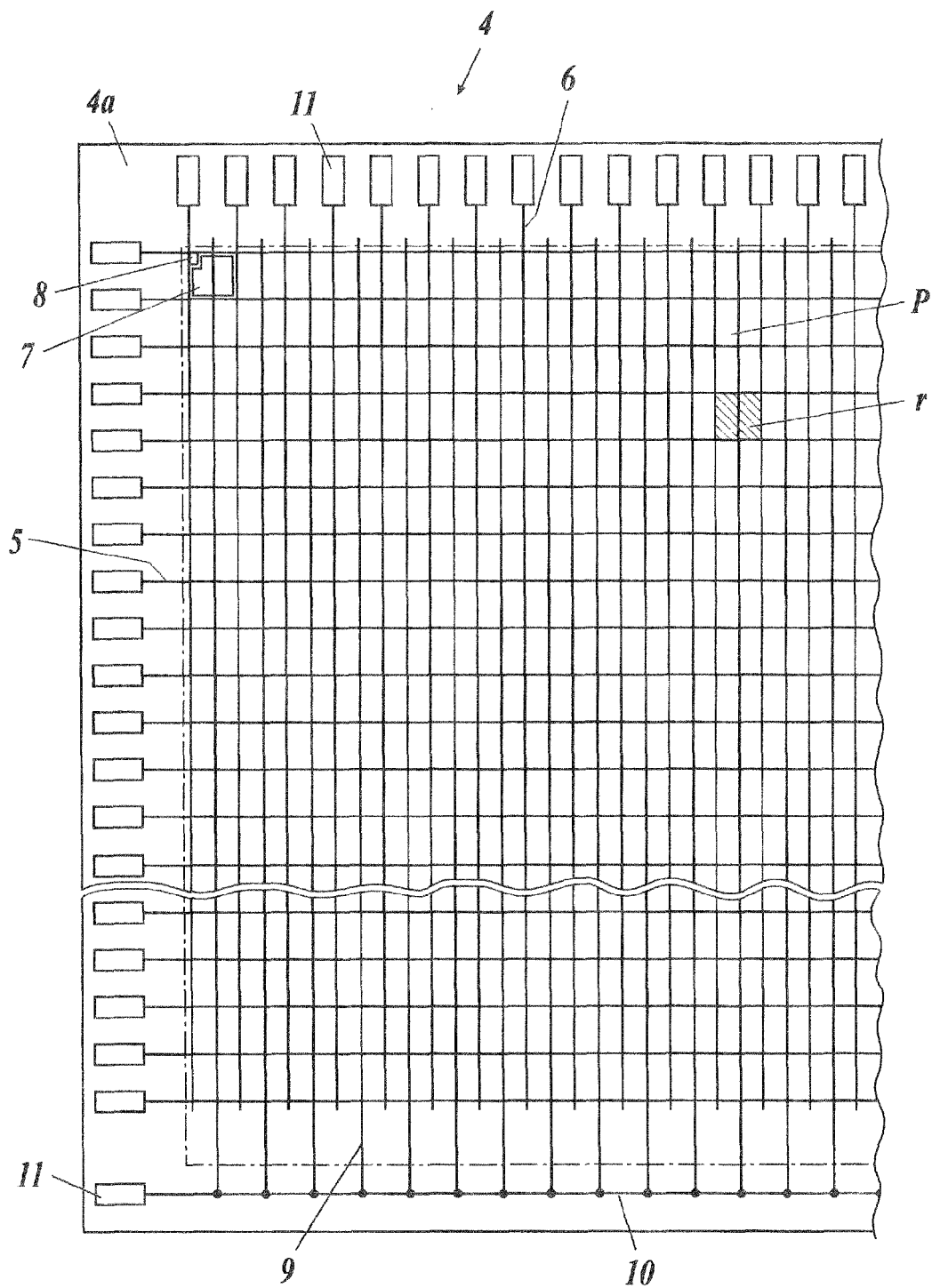
FIG. 5 This is a plane view showing a configuration of a substrate of the radiographic image capturing apparatus.

In the embodiment, the substrate 4 is formed of a glass substrate, and a plurality of scanning lines 5 and a plurality of signal lines 6 are arranged so as to intersect each other on the surface 4a which is the side of the substrate 4 facing the scintillator 3 as shown in FIG. 5. Radiation detection elements 7 are provided respectively in the sections r which are defined by the plurality of scanning lines 5 and the plurality of signal lines 6 on the surface 4a of the substrate 4.

In such way, the entire sections r in which a plurality of radiation detection elements 7 are respectively provided, the plurality of radiation detection elements 7 being arranged in two dimensional manner, in the sections r defined by the scanning lines 5 and the signal lines 6, that is the region indicated by dashed line in FIG. 5, is the detection unit P.

Although photodiodes are used as the radiographic detection elements 7 in the embodiment, photo-transistors or the like can be used, for example, other than photodiodes. As shown in the after mentioned FIG. 7, each of the radiation detection elements 7 is connected with a source electrode 8c of a TFT 8 which is a switching unit. Further, a drain electrode 8d of the TFT 8 is connected to a signal line 6.

Then, the TFT 8 is turned ON when ON voltage is applied to the gate electrode 8g from the after-mentioned scanning drive unit 15 via a scanning line 5 and electric charges accumulated in the radiation detection element 7 are released into a signal line 6 via the source electrode 8s and the drain electrode 8d. Further, the TFT 8 is turned OFF when OFF voltage is applied to the gate electrode 8g via the connected scanning line 5, and the releasing of electric charges to the signal line 6 from the radiation detection element 7 is stopped to hold electric charges in the radiation detection element 7.

In the embodiment, a plurality of radiation detection elements 7 which are aligned in a column are connected to a bias line 9. As shown in FIG. 5, the bias lines 9 are connected to one hard wiring 10 at their respective positions outside of the detection unit P of the substrate 4.

Figure 6:
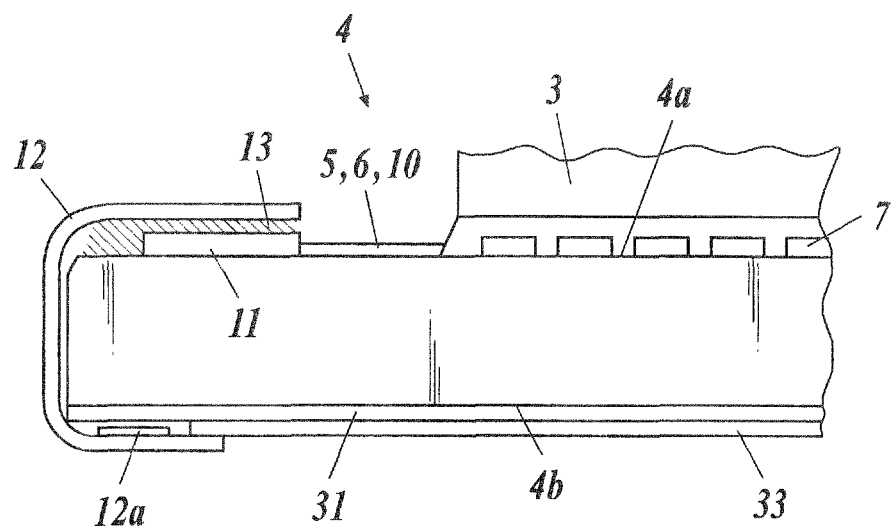
FIG. 6 This is a side view for explaining a substrate on which COF, PCB substrate and the like are attached.

Moreover, each of the scanning lines 5, each of the signal lines 6 and the hard wiring 10 of bias lines 9 are connected respectively to input/output terminals (also called pads) which are provided near edge sections of the substrate 4. As shown in FIG. 6, each of the input/output terminals 11 is connected with the COF (Chip On Film) 12 in which a chip such as an IC 12a is embedded on a film via an anisotropic conductive adhesive 13 such as an anisotropic conductive film and anisotropic conductive paste.

Further, the COF 12 is drawn around to the back surface 4b of the substrate 4 and is connected to the above-mentioned PCB substrate 33 at the back surface 4b. In such way, the section of substrate 4 of the sensor panel SP of the radiographic image capturing apparatus 1 is formed. Here, in FIG. 6, electronic components 32 are omitted in the drawing.

Here, a circuit configuration of the radiographic image capturing apparatus 1 will be described by using FIG. 7. With respect to each of the radiation detection elements 7, one electrode thereof is connected to a bias line 9 and the bias line is connected with the hard wiring 10 to be connected with the bias power supply 14. The bias power supply 14 applies bias voltage (reverse-bias voltage in the embodiment) to an electrode of each of the radiation detection elements 7 via the hard wiring 10 and a bias line 9.

Further, the other electrode of each of the radiation detection elements 7 is connected to the source electrode 8s (indicated by S in FIG. 7) of a TFT 8. The gate electrodes 8g (indicated by G in FIG. 7) of the TFTs 8 are connected to the lines L1 to Lx of the scanning lines 5 which extend from the gate driver 15b of the scanning drive unit 15. Moreover, the drain electrodes 8d (indicated by D in FIG. 7) of the TFTs 8 are connected to the signal lines 6.

The scanning drive unit 15 includes a power supply 15a which supplies ON voltage and OFF voltage to a gate driver 15b and the gate driver 15b which switches the voltage to be applied to the lines L1 to Lx of scanning lines 5 between ON voltage and OFF voltage. The gate driver 15b controls ON state and OFF state of the TFTs 8 by switching the voltage to be applied to the gate electrodes 8g of the TFTs 8 via the lines L1 to Lx of scanning lines 5 between ON voltage and OFF voltage.

Figure 28:
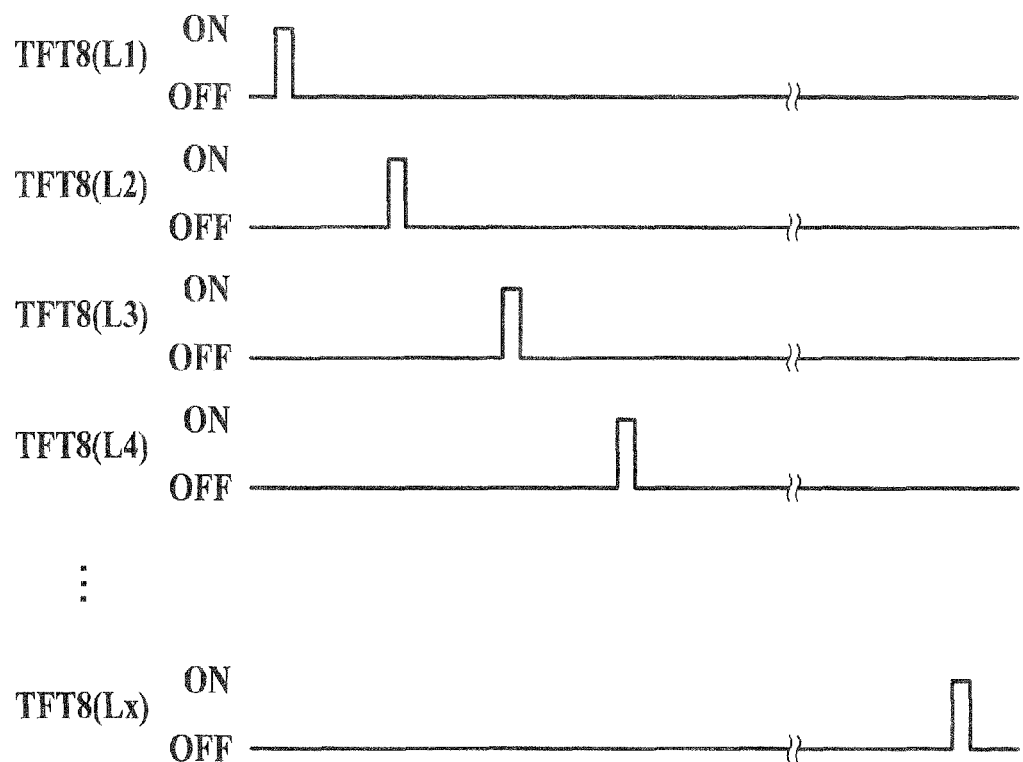
FIG. 28 This is a timing chart showing timing for applying ON voltage to each scanning line in the read-out processing of image data performed in a FPD type radiographic image capturing apparatus.

Then, in read-out processing to be performed after radiographic image capturing is carried out by emitting radiation to the radiographic image capturing apparatus 1 via a subject, the gate driver 15b of the scanning drive unit 15 sequentially applies ON voltage to the lines L1 to Lx of scanning lines 5 as shown in FIG. 28, for example, so that electric charges accumulated in radiation detection elements 7 due to radiation irradiation are to be released to the signal lines 6.

The signal lines 6 are connected respectively to the read-out circuits 17 which are formed in the read-out IC 16. Each of the read-out circuits 17 includes an amplifier circuit 18, a correlated double sampling circuit 19, an analog multiplexer 21 and an A/D converter 20.

At the time of radiographic image capturing, when a radiographic image capturing apparatus 1 is irradiated with radiation via a subject, the radiation is converted into electromagnetic waves of other wavelength by the scintillator 3 and the radiographic detection elements 7 right below the scintillator 3 are to be irradiated with the converted electromagnetic waves. Then, electric changes are generated in the radiation detection elements 7 according to their radiation dose (that is, amount of light of electromagnetic waves) of irradiation.

Thereafter, in read-out processing of pieces of image data D from the radiation detection elements 7, when ON voltage is applied to a predetermined line Ln in the scanning lines 5 from the gate driver 15b of the scanning drive unit 15 as described above, ON voltage is applied to the gate electrodes 8g of the TFTs 8 which are connected to the line Ln of the scanning lines 5 through the line Ln and the TFTs 8 are turned ON and electric charges are released into signal lines 6 through the TFTs 8 from the radiation detection elements 7 which are connected to the TFTs 8 which are turned ON.

Then, voltage values are output from the amplifier circuits 18 according to the amounts of electric charges released from the radiation detection elements 7, correlated double sampling is performed on the output voltage values in the correlated double sampling circuits 19 and pieces of image data D in analog values are output to the multiplexer 21. The pieces of image data D which are sequentially output from the multiplexer 21 are sequentially converted into pieces of image data D in digital values in the A/D converter 20 and the pieces of image data D in digital values are output to the storage section 23 to be stored sequentially.

The control unit 22 includes a CPU (Central Processing Unit), a ROM (Read Only Memory), a RAM (Random Access Memory), a computer in which an input/output interface or the like is connected to a bus, a FPGA (Field Programmable Gate Array) and such like. The control unit 22 may be configured with a specialized control circuit.

The control unit 22 controls operations and the like of functional units of the radiographic image capturing apparatus 1 such as the scanning drive unit 15 and the read-out circuits 17. The storage unit 23 consists of a DRAM (Dynamic RAM) and the like and a battery 24 which supplies power to each functional unit of the radiographic image capturing apparatus 1 are connected to the control unit 22. Further, the above-mentioned antenna device 41 is connected to the control unit 22.

When radiographic image capturing is carried out, the control unit 22 performs the read-out processing to read out electric charges, that is, pieces of image data D from the radiation detection elements 7 in the way described above. Further, in the embodiment, the control unit 22 creates thinned data Dt for preview by thinning each of the pieces of image data D at a predetermined rate on the basis of the pieces of image data D which are read out from the radiation detection elements 7 and stored in the storage unit 23.

In the embodiment, when radiographic image capturing is completed and pieces of image data D are read out from the radiation detection elements 7 and stored in the storage unit 23, the control unit 22 promptly creates pieces of thinned data Dt and sends the pieces of thinned data Dt to the after-mentioned radiographic image processing apparatus 70.

Here, in the embodiment, when a radiographic image capturing apparatus 1 is loaded in the bucky 51, the control unit 22 sends pieces of thinned data Dt, pieces of image data D and the like to the radiographic image processing apparatus 70 via the bucky 51, and when a radiographic image capturing apparatus 1 is not loaded in the bucky 51 and is used alone, the control unit 22 sends pieces of thinned data Dt and the like via the antenna device 41.

For example, pieces of thinned data Dt can be created by extracting image data D of one pixel for every 3×3 pixels or 4×4 pixels when pieces of image data D are aligned corresponding to the radiation detection elements 7 aligned in two dimensional manner. Alternatively, pieces of thinned data Dt can be created by extracting pieces of image data D from the radiation detection elements 7 which are connected to the line Ln in every predetermined interval such as extracting pieces of image data D from the radiation detection elements 7 which are connected to the lines L1, L4, L7 . . . of the scanning lines 5.

Further, in the embodiment, the control unit 22 automatically sends the corresponding pieces of image data D which the thinned data Dt was based on to the radiographic image processing apparatus 70 after sending the pieces of thinned data Dt to the radiographic image processing apparatus 70.

On the other hand, in the embodiment, because the control unit 22 obtains off-set correction values O for correcting off-set caused by dark charge superimposed on the image data D obtained in radiographic image capturing every time the one time radiographic image capturing is completed or when a series of radiographic image capturing is completed, so-called dark reading processing is performed automatically. Here, dark reading processing can be performed before each radiographic image capturing starts or before a series of radiographic image capturing starts.

In dark reading processing, after the TFTs 8 of the radiographic image capturing apparatus 1 are turned off and left as they are for a predetermined time period without the radiographic image capturing apparatus 1 being irradiated by radiation, similarly to the above described read-out processing, dark charges which are accumulated in the radiation detection elements 7 are read out as dark read values d and are stored in the storage unit 23.

Then, the control unit 22 sets the read out dark read values d of the radiation detection elements 7 as off-set correction values O or performs the dark reading processing for a plurality of times and obtains an average of the plurality of dark read values d obtained from the radiation detection elements 7 so as to calculate off-set correction values O and sends the calculated off-set correction values O to the radiographic image processing apparatus 70.

Next, each device and the like in the radiographic image capturing system 50 will be described.

As shown in FIG. 1, with respect to a bucky 51, a portable type radiographic image capturing apparatus 1 can be used by being loaded in a cassette holding unit (also called cassette holder) 51a in the embodiment. In the embodiment, although a bucky 51A and a bucky 51B for standing position image capturing and recumbent position image capturing, respectively, are provided as the bucky 51 in the image capturing room Ra as shown in FIG. 1, only either one of the buckies may be provided.

In the embodiment, when a radiographic image capturing apparatus 1 is to be used by being loaded in the bucky 51, the connector 51b which is provided at the end of a cable that extends from the bucky 51 is to be connected to the connector 39 of the radiographic image capturing apparatus 1 before the radiographic image capturing apparatus 1 is to be loaded in the bucky 51.

Here, configuration may be such that the connector 51b is provided in the cassette holding unit 51a of the bucky 51 and the connector 39 of the radiographic image capturing apparatus 1 and the connector 51b connect automatically when the radiographic image capturing apparatus 1 is loaded in the cassette holding unit 51a, for example.

As shown in FIG. 1, at least one radiation source 52 for emitting radiation onto a subject is provided in the image capturing room Ra. In the embodiment, in the radiation source 52, the radiation source 52A is hung from the ceiling of the image capturing room Ra, for example, and radiation can be emitted onto the radiographic image capturing apparatus 1 which is loaded in the bucky 51A for standing position image capturing or the bucky 51B for recumbent position image capturing by changing it's emitting direction and the like.

Moreover, in the embodiment, a portable radiation generation device 52B is also provided and the portable radiation generation device 52B can be carried to any place within the image capturing room Ra and emit radiation in an arbitrary direction. Further, radiation can be emitted from the portable radiation generation device 52B in a state where the radiographic image capturing apparatus 1 alone, without being loaded in the bucky 51, is held against a part of the body of a patient which is a subject or is inserted between the bucky 51B for recumbent position image capturing or the bed which is not shown in the drawing and the body of a patient.

In the image capturing room Ra, a base station 54 including a wireless antenna 53 which relays communication between the radiographic image capturing apparatus 1 and the radiographic image processing apparatus 70 is provided. Here, in the embodiment, the bucky 51 and the base station 54 are connected with a cable or the like and thinned data Dt and the like output from the radiographic image capturing apparatus 1 is to be sent to the radiographic image processing apparatus 70 via the bucky 51, the base station 54 and the like when the radiographic image capturing apparatus 1 is to be used by being loaded in the bucky 51.

Moreover, a cradle 55 is connected to the base station 54. The cradle 55 may be set in either of the image capturing room Ra and the front room Rb and is to be set at a position where the radiation emitted from the radiation generation device 52 does not reach, that is, at a position in a corner of the image capturing room Ra, for example, when it is to be set in the image capturing room Ra.

As shown in FIG. 1, an operation table 57 of the radiation generation device including an exposure switch 56 for instructing the radiation source 52 to start emission of radiation and the like is provided in the front room (also called operation room) Rb. Radiation is to be emitted onto the radiographic image capturing apparatus 1 from the radiation source 52 by an operator such as a radiologist operating the exposure switch 56.

Further, as described above, the radiographic image processing apparatus 70 is provided in the front room Rb and the radiographic image processing apparatus 70 is configured by including a CPU, a ROM, a RAM, a computer in which an input/output interface or the like is connected to a bus and the like which are not shown in the drawing in the embodiment. Predetermined programs are stored in the ROM and the radiographic image processing apparatus 70 executes various types of processing in compliance with the programs by reading out the needed programs and expanding the programs in the work region in the RAM.

The radiographic image processing apparatus 70 is provided with a display unit 70a formed of a LCD (Liquid Crystal Display) or the like and further, input units such as a keyboard, mouse and the like which are not shown in the drawing are connected to the radiographic image processing apparatus 70. Moreover, a storage unit 70b formed of a hard disk or the like is connected to the radiographic image processing apparatus 70 and further, although omitted in the drawing, another computer and an external device such as an imager which records and outputs a radiographic image on an image recording medium such as a film on the basis of image data output from the radiographic image processing apparatus 70 are connected with the radiographic image processing apparatus 70 via a LAN or the like.

In the embodiment, when thinned data Dt is sent from the radiographic image capturing apparatus 1 as described above, the radiographic image processing apparatus 70 displays a preview image in the display unit 70b on the basis of the thinned data Dt. Such displaying of preview image is to confirm whether radiation image capturing was performed normally and to determine whether re-capturing of image is needed by an operator such as a radiologist looking at the preview image. When an operator determines that re-capturing of image needs to be performed, the radiographic image capturing is to be performed again.

Further, when an operator determines that re-capturing of image is not needed and an input indicating that image processing is to be performed on this radiographic image capturing is input to the radiographic image processing apparatus 70, the radiographic image processing apparatus 70 is to perform image processing on the image data D obtained in this radiographic image capturing.

Figure 9:
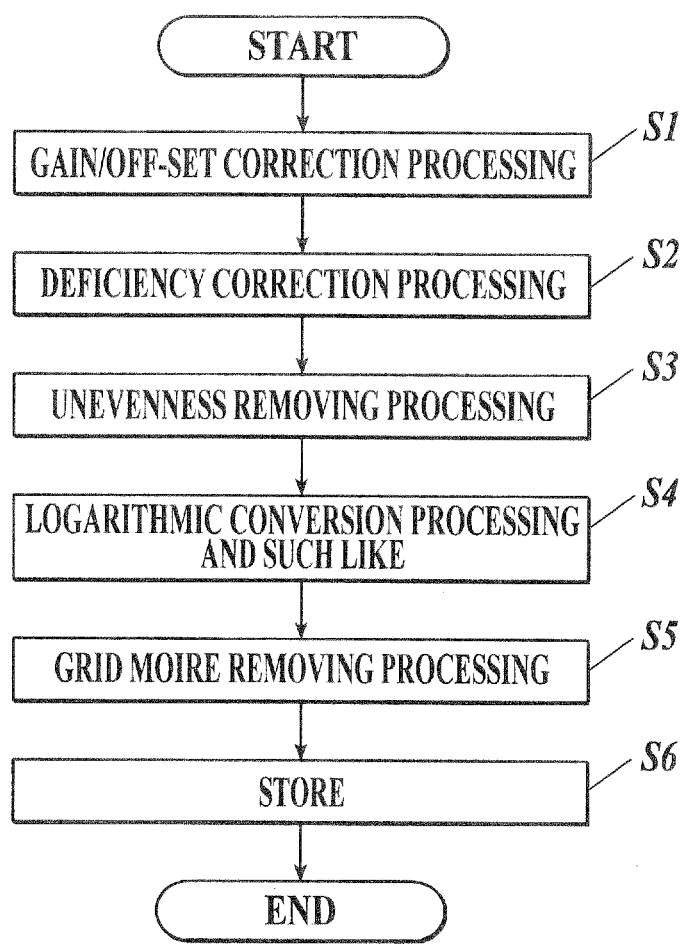
FIG. 9 This is a flowchart showing a procedure of image processing performed on image data in the radiographic image processing apparatus according to the embodiment.

In the embodiment, the radiographic image processing apparatus 70 performs image processing on image data D according to the flowchart shown in FIG. 9.

Figure 10:
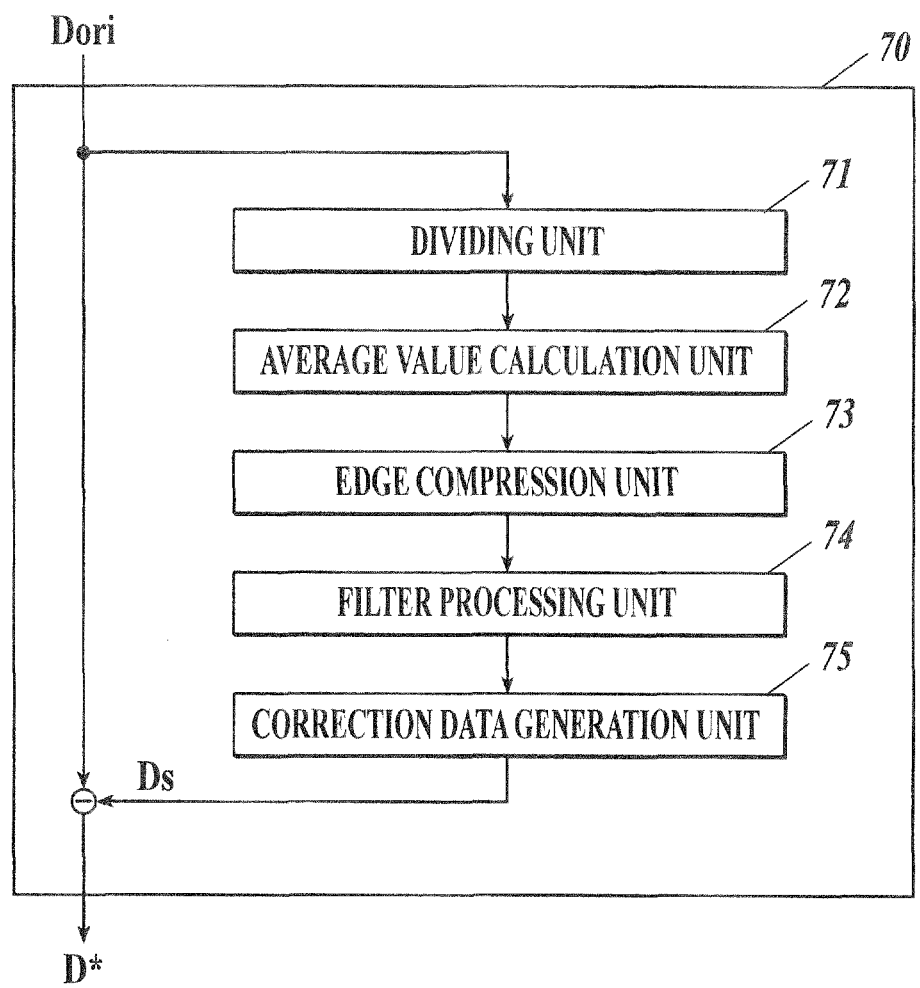
FIG. 10 This is a block diagram showing a functional configuration of the radiographic image processing apparatus.

As shown in FIG. 10, the radiographic image processing apparatus 70 functionally includes at least a dividing unit 71, an average value calculation unit 72, an edge compression unit 73, a filter processing unit 74 and a correction data generation unit 75.

In the unevenness removing processing (step S3) of FIG. 9, correction data Ds consisted only of the above mentioned streaky unevenness components (see FIG. 29) is generated from image data D (that is, the after-mentioned original image data Dori) on which pre-processing is performed as described later by the above units 71 to 75, and pieces of image data D* in which streaky unevenness is removed are generated by subtracting it's corresponding correction data Ds from each of the pieces of original image data Dori.

Hereinafter, the image processing to be performed on image data D in the radiographic image processing apparatus 70 will be described in detail. Further, operation of the radiographic image processing apparatus 70 according to the embodiment will be described.

Here, the processing characteristic to the present invention is the unevenness removing processing (step S3) as described above, and because other processes are known processes performed in a normal image processing performed on image data D obtained in radiographic image capturing, their descriptions are simplified or omitted.

As described above, when a piece of image data D (that is, so-called raw data) and off-set correction value O are sent from the radiographic image capturing apparatus 1 with respect to each radiation detection element 7 as described above, the radiographic image processing apparatus 70 stores the piece of data in the storage unit 70b and performs gain/off-set correction processing (step S1) first.

In the gain/off-set correction processing (step S1), the radiographic image processing apparatus 70 reads out the gain correction value G for each radiation detection element 7 in the radiographic image capturing apparatus 1 stored in the storage unit 70b and calculates original image data Dori with respect to each radiation detection element 7 on the basis of each piece of image data D according to the following formula (1).

$$Dori = G \times (D - O) \quad (1)$$

Here, original image data Dori is image data which is the base for generating correction data Ds in the unevenness removing processing (step S3) and is image data which is the base for generating each piece of image data D* in which streaky unevenness is removed by the generated correction data being subtracted.

Next, in the deficiency correction processing (step S2), the radiographic image processing apparatus 70 refers to the defected pixel map stored in the storage unit 70b and performs correction of defected pixels. Here, defected pixel is a radiation detection element 7 from which abnormal image data D is read out or the abnormal image data read out from the radiation detection element 7.

In the deficiency correction processing (step S2), the radiographic image processing apparatus 70 refers to the defected pixel map and invalidates and discards the original image data Dori of an abnormal radiation detection element 7 shown on the map as a defected pixel. Further, the radiographic image processing apparatus 70 performs linear interpolation or the like with original image data Dori of a normal radiation detection element 7 adjacent to the abnormal radiation detection element 7 in the detection unit P so as to set as the original image data Dori of the abnormal radiation detection element 7.

Next, the radiographic image processing apparatus 70 performs the unevenness removing processing (step S3) characteristic to the present invention. Here, it is preferred that the unevenness removing processing (step S3) is performed after the gain/off-set correction processing (step S1) and the deficiency correction processing (step S2) as described above.

If the unevenness removing processing is to be performed after the after-mentioned logarithmic conversion processing and such like (step S4), value differences are amplified with respect to the pieces of original image data Dori having relatively small values among the pieces of original image data Dori calculated according to the above formula (1) and value differences are compressed with respect to the pieces of original image data Dori having relatively large values among the pieces of original image data Dori calculate according to the above formula (1). Therefore, streaky unevenness is hard to be corrected. Thus, it is preferred that the unevenness removing processing (step S3) is performed before the logarithmic conversion processing and such like (step S4).

The unevenness removing processing (step S3) is processing where pieces of correction data Ds consisted only of the streaky unevenness (see FIG. 29) components are created from pieces of original image data Dori as described above by the units including the dividing unit 71 to the correction data generation unit 75 performing their processing, and pieces of image data D* in which streaky unevenness is removed are generated by subtracting it's corresponding piece of correction data Ds from each piece of original image data Dori.

Figure 11:
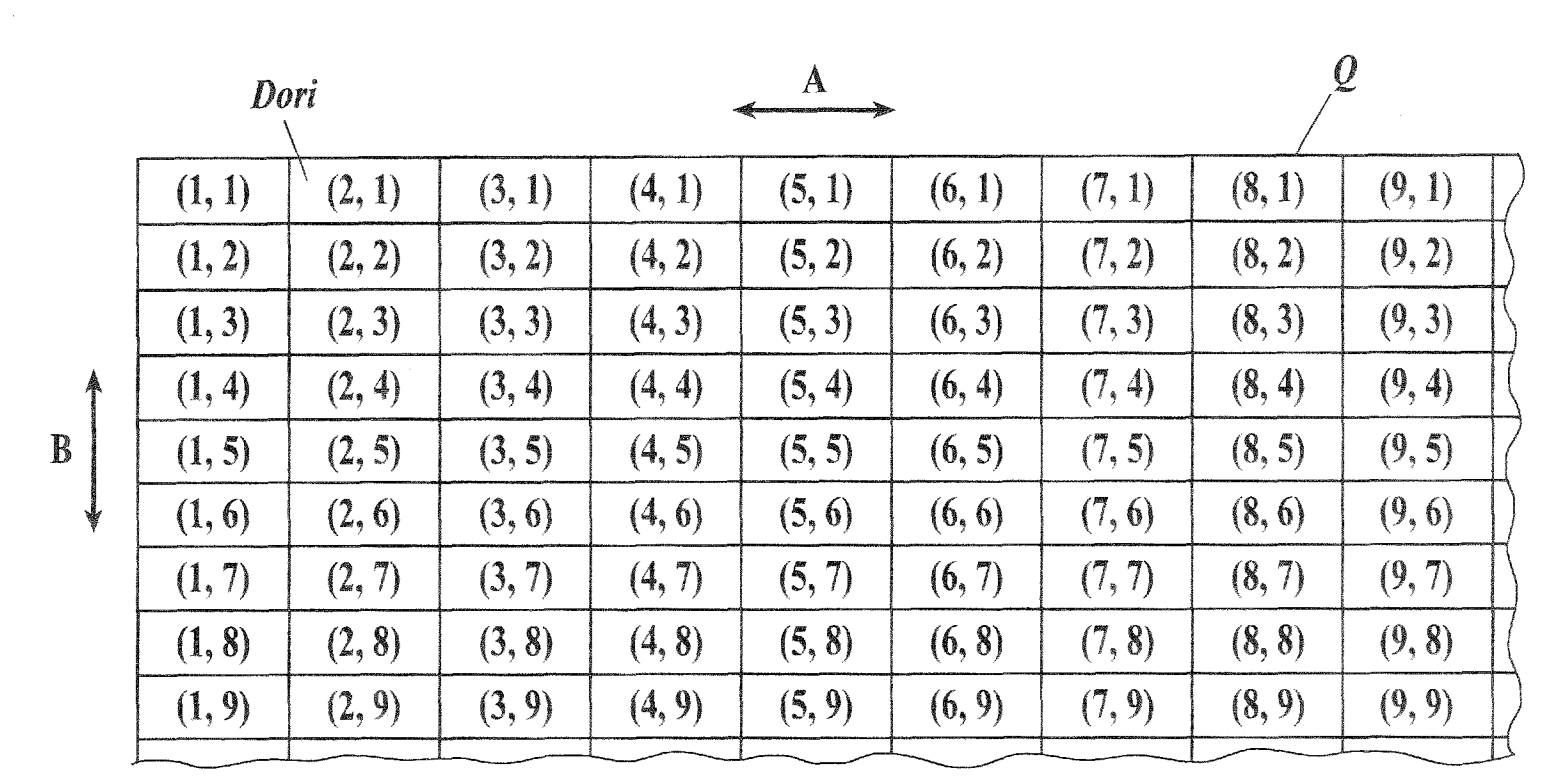

First, as a premise for generating correction data Ds, pieces of original image data Dori are arranged in two dimensional manner so as to correspond respectively with the plurality of radiation detection elements 7 which are arranged in two dimensional manner on the detection unit P (see FIGS. 5 and 7) as shown in FIG. 11.

Here, a piece of original image data Dori corresponding to a radiation detection element 7 $(m, n)$ at a position where the $m^{th}$ signal line 6 and the $n^{th}$ scanning line (that is, line Ln of scanning lines 5) intersect each other on the detection unit P is expressed as Dori (m, n). Further, in FIG. 11, a piece of original image data Dori (m, n) is merely expressed as (m, n).

Further, when pieces of original image data Dori (m, n) are arranged as shown in FIG. 11, the extending direction of the scanning lines 5 (hereinafter, called scanning line direction) on the detection unit P is indicated by an arrow A in the drawing and the extending direction of the signal lines 6 (hereinafter, called signal line direction) is indicated by an arrow B in the drawing.

Figure 12:
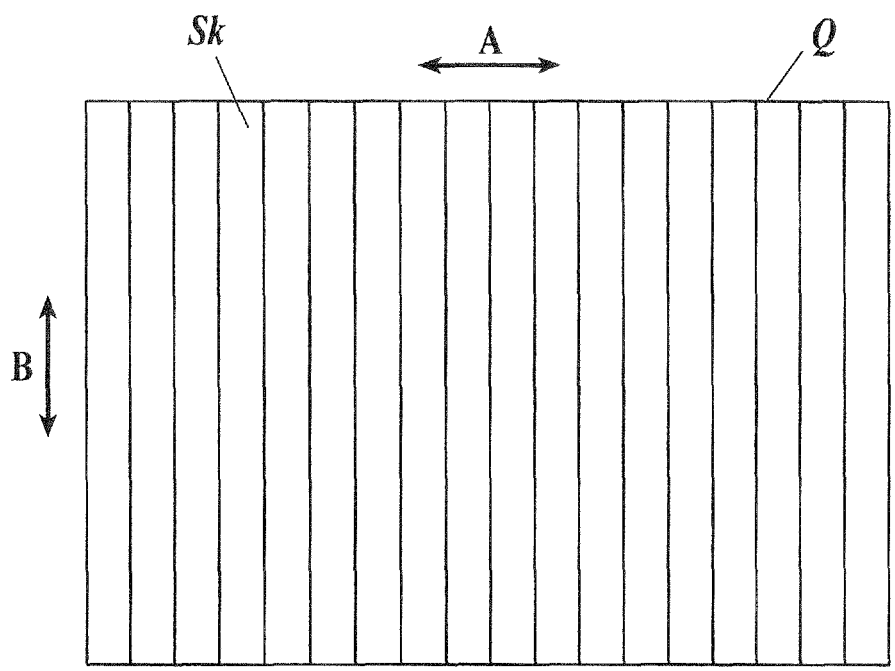
FIG. 12 This is a diagram for explaining section areas formed by dividing the region of original image data.

The dividing unit 71 of the radiographic image processing unit 70 divides the region Q in which the pieces of original image data Dori (m, n) are arranged in two dimensional manner as shown in FIG. 11 in section areas Sk by sectioning in units of a predetermined number of pieces of original image data Dori at least in the scanning line direction A as shown in FIG. 12.

The predetermined number of pieces of original image data Dori in a section area Sk along the scanning line direction A is set to an arbitrary number, and for example, it is set to 20 pieces or the like. Further, as shown in FIG. 12, the signal line direction B of a section area Sk can be the entire pieces of original image data Dori along the signal line direction B in the region Q or the region Q can also be divided in section areas Sk in the signal line direction B by sectioning in units of a predetermined number of pieces of original image data Dori in the signal line direction B.

Figure 13:
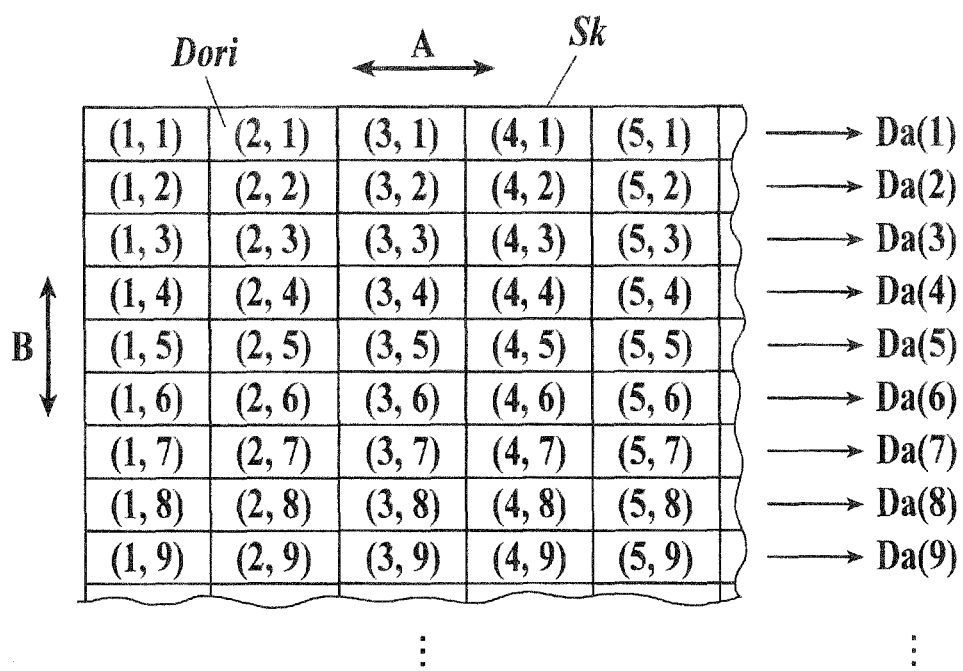
FIG. 13 This is a diagram for explaining calculation processing of an average value of pieces of original image data aligned in the extending direction of a same scanning line in a section area.

As shown in FIG. 13, the average value calculation unit 72 of the radiographic image processing apparatus 70 calculates an average value Da of pieces of original image data Dori (m, n) aligned in the extending direction of the line Ln of the same scanning line 5 among the pieces of original image data Dori (m, n) in each section area Sk formed by the dividing unit 71 dividing the region Q. Then, this processing is performed for each of the lines L1 to lx (see FIG. 7) in the scanning lines 5.

Figure 14:
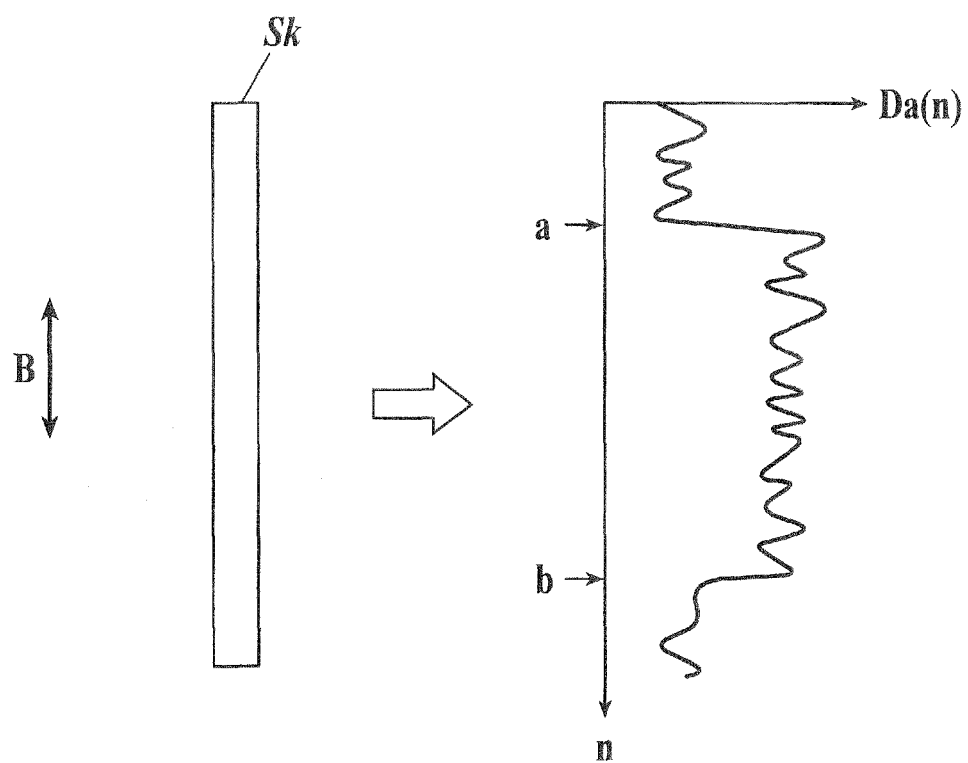
FIG. 14 This is a diagram showing an example of signal line extending direction profile of average values when the calculated average values are aligned along the extending direction of signal lines.

In such way, when average values Da of the pieces of original image data Dori (m, n) along the scanning line direction A are calculated, each of the average values Da is the value for each of the lines L1 to lx the scanning lines 5 and is a variable number of the line number n. Therefore, hereinafter, the average value Da of a line Ln of scanning lines 5 is expressed as Da(n). Further, when the average values Da(n) are aligned in the signal line direction B, a profile of the average values Da(n) in the signal line direction B is obtained as shown in FIG. 14. Further, calculation of average values Da (n) is performed for each of the section regions Sk.

Figure 15:
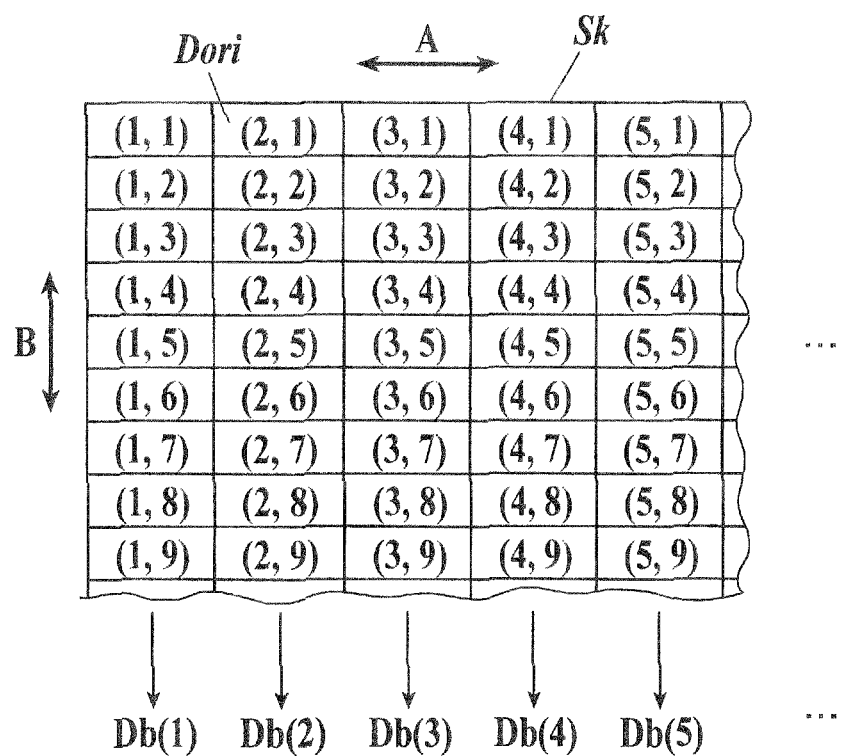
FIG. 15 This is a diagram for explaining a case where an average value of pieces of original image data aligned in the extending direction of a same signal line in a section area is calculated.
Figure 29:
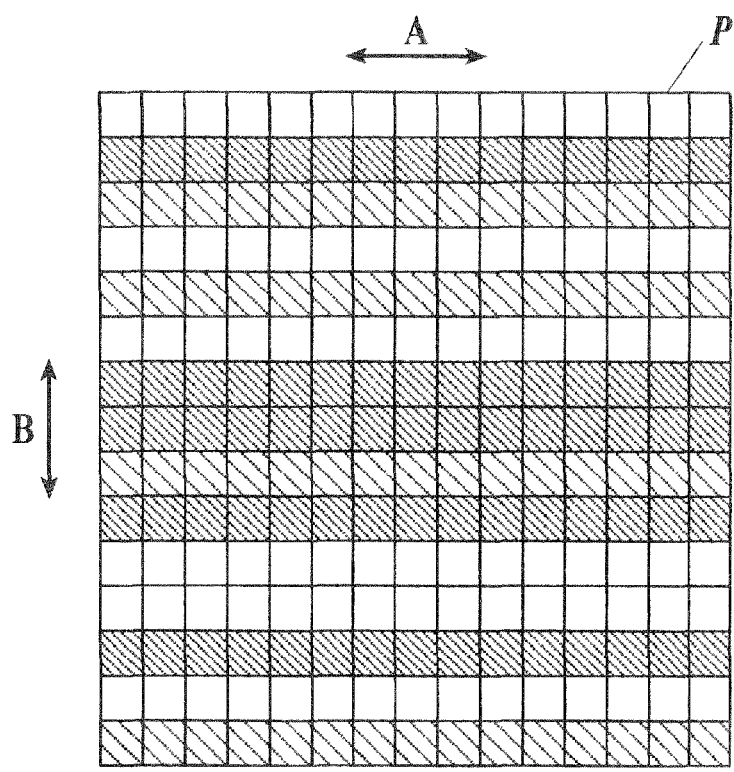
FIG. 29 This is a diagram showing streaky unevenness which extends in the extending direction of scanning lines that appears in a radiographic image generated on the basis of image data captured with a FPD type radiographic image capturing apparatus.

As shown in FIG. 29, when a FPD type radiographic image capturing apparatus 1 as in the embodiment is used, streaky unevenness that extends in the scanning line direction A characteristically appears. In such condition, if average values Db(m) of pieces of original image data Dori (m, n) in the signal line direction B are to be calculated as shown in FIG. 15 hypothetically when calculating average values of pieces of original image data Dori (m, n) as described above, streaky unevenness components cannot be extracted from the pieces of original image data Dori because the streaky unevenness components that extend in the scanning line direction A cancel each other out when calculating the average values Db(m).

In view of such problem, when average values Da of pieces of original image data Dori (m, n) in the scanning line direction A are calculated as shown in FIG. 13, streaky unevenness components that extend in the scanning line direction A do not cancel each other out when calculating the average values Da(n) and the streaky unevenness components can be extracted from the pieces of original image data Dori because the streaky unevenness components remain as they are in the calculated average values Da(n).

Here, not only the streaky unevenness components but also various types of noise components are superimposed on the pieces of original image data Dori on which merely the gain/off-set processing (step S1 of FIG. 9) and the deficiency correction processing (step S2) are performed. However, by calculating the average values Da of pieces of original image data Dori (m, n) in the scanning line direction A as described above, although the streaky unevenness components remain, other various types of noises are decreased because they cancel each other out.

Therefore, by calculating the average values Da of pieces of original image data Dori (m, n) in the scanning line direction A, the average values Da will be data mainly including the streaky unevenness components as noise components.

Moreover, when a signal line direction B profile of the average values Da(n) is obtained as described above, average values Da(n) have different values between the parts where internal organs, bones and the like in the body of a patient is captured, for example, and other parts. FIG. 14 shows a case where the average values Da(n) of the part where an internal organ or a bone is captured has large values comparing to the average values Da(n) of other part.

Next, the edge compression unit 73 of the radiographic image processing apparatus 70 generates a profile in which the differences in average values Da(n) that occur at the border of a target which is an internal organ, a bone or the like in the body of a patient captured and the surrounding thereof are compressed for each section area Sk with respect to the signal line direction B profile of the average values Da(n) calculated for each section region Sk as described above.

In particular, when the signal line direction B profile of the average values Da(n) calculated for each section area Sk as described above is seen in an order from n having small value, for example, if the absolute value |Da(n)−Da(n−1)| of the difference Da(n)−Da(n−1) which is calculated by subtracting an average value Da(n−1) from an average value Da(n), the average value Da(n−1) being the value just before the average value Da(n), is greater than the threshold ΔDath which is pre-set, the profile in which differences are compressed is created by subtracting the above difference from the average value Da(n) and each of the average values Da(n), Da(n+1), Da(n+2), . . . thereafter. Hereinafter, the average values after the differences are compressed are indicated as averages values DA(n) to distinguish from the average values Da(n).

That is, when the signal line direction B profile of the average values Da(n) in the section area Sk is calculated as shown in FIG. 14, for example, and when the profile is seen in an order from n having small value, for example, average values Da(n) change drastically at the points n=a and n=b. Further, for example, at the point n=a, the absolute value |Da(a)−Da(a−1)| of the difference Da(a)−Da(a−1) which is calculated by subtracting the average value Da(a−1) from the average value Da(a), the average value Da(a−1) being the value just before the average value Da(a), becomes larger than the threshold ΔDa which is pre-set.

Therefore, the edge compression unit 73 calculates the average values DA(a) of after compression by subtracting the difference Da(a)−Da(a−1) from each of the average value Da(a) and the average values Da(a+1), Da(a+2), . . . thereafter.

In such case, for example, when the difference Da(a)−Da(a−1) is subtracted from the average value Da(a) at the point n=a, the average value DA(a) of after compression will be as shown bellow and will be equal to the average value Da(a−1) of n=a−1 just before.

$$DA(a)=Da(a)-(Da(a)-Da(a-1)) \therefore DA(n)=Da(a-1) \quad (2)$$

Further, as for the average values Da(a+1), Da(a+2), . . . the following subtraction processing are respectively performed and average values DA(a+1), DA(a+2), . . . of after compression are calculated.

$$DA(a+1)=Da(a+1)-(Da(a)-Da(a-1)) \quad (3)$$

$$DA(a+2)=Da(a+2)-(Da(a)-Da(a-1)) \quad (4)$$

Further, similar processing is performed on the average value Da(b) and each of the average values Da(b), Da(b+1), Da(b+2), . . . thereafter and the average values DA(b), DA(b+1), DA(b+2), . . . of after compression are calculated.

Figure 16:
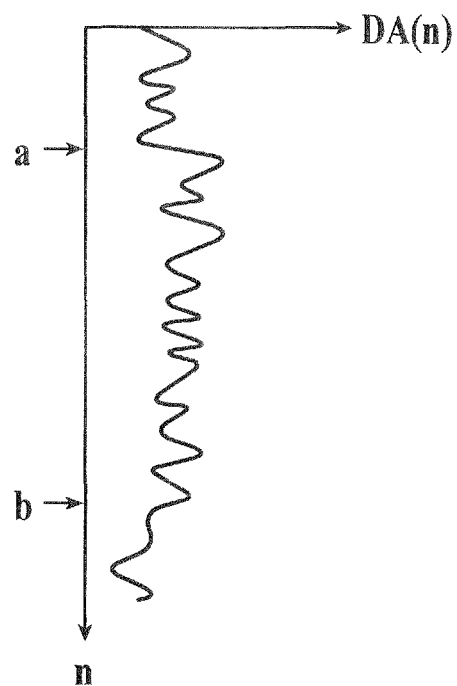
FIG. 16 This is a graph showing an example of signal line extending direction profile of average values after edge compression processing is performed.

By such processing being performed by the edge compression unit 73, a profile of average values DA(n) in which differences are compressed as shown in FIG. 16 is created from the profile of average values Da(n) in the section area Sk shown in FIG. 14, for example. The edge compression unit 73 performs such processing for each section area Sk.

In an image where an internal organ, a bone or the like in the body of a patient are captured as described above, values of adjacent average values Da(n) differ greatly at the border between the part where the internal organ, bones of the like is captured and the part where other parts are captured, that is, at the edge parts. On the other hand, although the streaky unevenness components also have different values between adjacent average values Da(n), the differences between adjacent average values Da(n) at the edge parts of the internal organ, bone or the like are drastically larger than the differences in case of streaky unevenness components.

Therefore, an appropriate value which can accurately distinguish between the differences in values between adjacent average values Da(n) at the edge parts of internal organ, bone or the like and the differences in values between adjacent average values Da(n) of streaky unevenness components is set as the threshold ΔDath.

By setting the threshold ΔDath as described above, streaky unevenness components remain in the profile of average values DA(n) of after compression without being subjected to the edge compression processing, and the edge parts of internal organ, bone or the like can be removed from the profile of average values DA(n) of after compression by being subjected to the edge compression processing.

In such way, by performing the edge compression processing, the edge parts of internal organ, bone or the like do not remain in the after-mentioned correction data Ds which is created on the basis of the profile of average values DA(n) of after compression, and further, the correction data Ds can be data only including streaky unevenness components.

Here, instead of performing the edge compression processing by the edge compression unit 73 of the radiographic image processing apparatus 70 on the basis of a difference Da(n)−Da(n−1) calculated by subtracting an average value Da(n−1) from an average Da(n) as described above, configuration may be such that the edge compression processing is performed by a so-called dynamic compression processing where low-frequency components in the profile of average values Da(n) are compressed, for example.

Further, for example, configuration may be such that an average value of average values Da(n) in a predetermined range such as n−5 to n+5 including the target n is calculated, the difference between the average value Da(n) at the target n and the average value of average values Da(n) within the predetermined range is calculated and edges are compressed as described above when the absolute value of the difference exceeds the pre-set threshold.

In such way, it is sufficient that the edge compression processing performed by the edge compression unit 73 appropriately generates a profile in which differences in average values Da(n) that occurs at the border between an subject such as internal organ, bone or the like in the body of a patient captured and the surrounding thereof with respect to the signal line direction B profile of average values Da(n) calculated for each section area Sk as described above and the specific method is not limited in anyway.

Next, the filter processing unit 74 of the radiographic image processing apparatus 70 performs processing to apply an adaptive filter on the profile of average values DA(n) of after compression which is created as described above for each section area Sk.

In the embodiment, a wiener filter is used as an adaptive filter. As it is well known, wiener filter is an adaptive filter which makes a square error between true data in which noise is not superimposed and data in which noise is superimposed minimum, and wiener filter is expressed as the following formula (5), for example.

[Formula 1]

$$Df(n) = DAave + \frac{\sigma^2(n) - \sigma^2 v}{\sigma^2(n)}(DA(n) - DAave) \quad (5)$$

Here, Df(n) represents a value of data after the filter processing, DAave represents an average value of average values DA(n) of after compression of the section area Sk, σv² represents a variance which is pre-set and σ²(n) represents a variance of DA(n). That is, the variance σ²(n) of DA(n) is the total sum Σ(DA(n)−DAave)² of (DA(n)−DAave)² within the micro range (for example, a range of n−5 to n+5) including n.

Then, when the variance $\sigma^2(n)$ of DA(n) is extremely larger comparing to the variance $\sigma v^2$ (that is, if $\sigma^2(n) \gg \sigma v^2$), the above formula (5) will be $$Df(n) \approx DA(n) \quad (6)$$

and data DF(n) of after filter processing will be a value close to the original average values DA(n) of after compression.

Further, when the variance $\sigma^2(n)$ of DA(n) is about the same as the variance $\sigma v^2$ (that is, if $\sigma^2(n) \approx \sigma v^2$), the above formula (5) will be $$Df(n) \approx -DAave \quad (7)$$

and data Df(n) of after filter processing will be a value close to the average value DAave of average values DA(n) of after compression.

Figure 17:
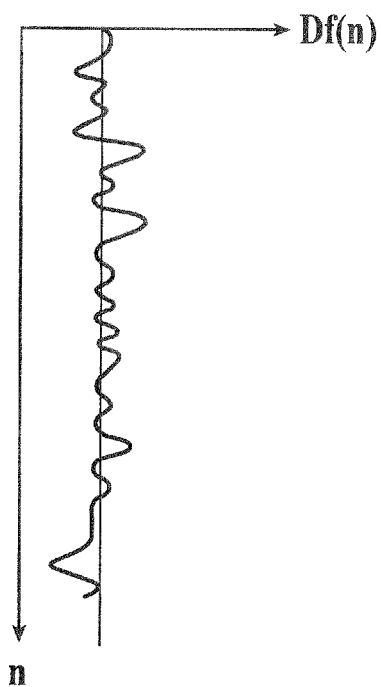
FIG. 17 This is a graph showing an example of signal line extending direction profile of pieces of data after filter processing is performed.

The data Df(n) of after filter processing calculated according to the abode formula (5) is the true data on which noises such as streaky unevenness and like of each of the section areas Sk are not superimposed and will be a profile as shown in FIG. 17.

On the other hand, correction data Ds consists only of streaky unevenness components (see FIG. 29) is what is desired to be obtained in the unevenness removing processing (step S3).

Therefore, by the filter processing unit 74 of the radiographic image processing apparatus 70 subtracting the data Df(n) of after filter processing (see FIG. 17) which is the true data calculated as described above, where noises such as streaky unevenness and the like are not superimposed, from the average values DA(n) of after compression shown in FIG. 16 according to the formula (8), data ds(n) which is to be the base for generating the correction data Ds of the section area Sk is calculated.

$$ds(n) = DA(n) - Df(n) \quad (8)$$

Hereinafter, the ds(n) is called correction data of each section area Sk.

In order to make the correction data ds(n) of each section area Sk be data only including streaky unevenness components, the variance $\sigma v^2$ to be set in advance in the above formula (5) needs to be set accurately. This can be realized by pre-setting the value of variance $\sigma v^2$ to a value about the same as the value of variance corresponding to the streaky unevenness.

That is, when the value of variance $\sigma v^2$ is set to a value about the same as the value of variance corresponding to the streaky unevenness, according to the above formula (5), it will be Df(n)≈DA(n) as shown in the above formula (6) when the variance $\sigma^2(n)$ of an average value DA(n) of after compression is extremely greater comparing to the variance $\sigma v^2$ (that is, variance corresponding to the streaky unevenness). When this is substituted in the above formula (8), the correction data ds(n) of each section area Sk will be about 0.

That is, a case where the variance $\sigma^2(n)$ of average values DA(n) calculated with respect to within the micro range of n−5 to n+5 including n, for example, is extremely greater comparing to the variance corresponding to the streaky unevenness which is the variance $\sigma v^2$ is the case where the average values DA(n) of after compression within the micro range are greater than the average value DAave of average values DA(n) of after compression as a whole or smaller as a whole. This means that long-period components caused by internal organ, bone or the like in the body of a patient, for example, are more dominant than the streaky unevenness components in the micro range.

Further, in order to make the correction data ds(n) of each section area Sk be data consists only of streaky unevenness components, it is preferred that long-period components other than the streaky unevenness components do not remain in the correction data ds(n) of each section area Sk. By setting the value of variance $\sigma v^2$ to a value about the same as the value of variance corresponding to the streaky unevenness, the correction data ds(n) of each section area Sk is to be about 0 within the micro range and long-period components other than the streaky unevenness components will not remain in the correction data ds(n) of each section area Sk. In such way, it is preferred to set the value of variance $\sigma v^2$ to a value about the same as the value of variance corresponding to the streaky unevenness.

Moreover, when the value of variance $\sigma v^2$ is set to a value close to the value of variance corresponding to the streaky unevenness, according to the above formula (5), it will be Df(n)≈DAave as shown in the above formula (7) when the variance $\sigma^2(n)$ of an average value DA(n) of after compression is about the same as the variance $\sigma v^2$ (that is, variance corresponding to the streaky unevenness) (that is, when $\sigma^2(n) \approx \sigma v^2$). When this is substituted in the above formula (8), the correction data ds of each section area Sk almost equals DA(n)−DAave.

That is, in such case, the correction data ds(n) of each section area Sk almost equals the streaky unevenness components included in the average values DA(n) of after compression and not 0. In such way, when the value of variance $\sigma v^2$ is set to a value about the same as the value of variance corresponding to the streaky unevenness, the correction data ds(n) of each section area Sk almost equals the streaky unevenness component when the micro range is a part where the streaky unevenness is reflected.

In order to make the correction data ds(n) of each section area Sk be data consists only of streaky unevenness components as described above, the streaky unevenness components need to remain accurately in the correction data ds(n) of each section area Sk at the parts in the profile where the streaky unevenness components are reflected. However, when the value of variance $\sigma v^2$ is set to a value about the same as the value of variance corresponding to the streaky unevenness as described above, the streaky unevenness components can be accurately remained in the correction data ds(n) of each section area Sk at the parts in the profile where the streaky unevenness components are reflected. Therefore, also in such respect, it is preferred that the value of variance $\sigma v^2$ is set to a value about the same as the value of variance corresponding to the streaky unevenness.

Here, how large in size the streaky unevenness components appear differ according to individual radiographic image capturing apparatuses 1. Therefore, the value of variance $\sigma v^2$ is set to an arbitrary value which can achieve the above object for each radiographic image capturing apparatus 1.

Figure 18:
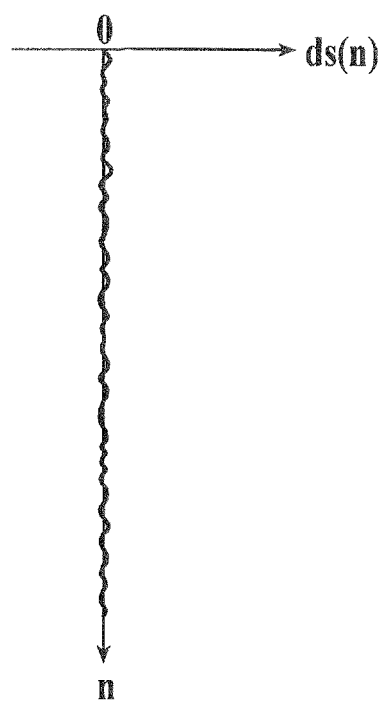
FIG. 18 This is a graph showing an example of signal line extending direction profile of correction data for each section area.

As described above, by using a wiener filter, correction data ds(n) of each section area Sk can be extracted accurately as shown in FIG. 18 even when high-pass filter processing or low-pass filter processing is not performed on the average values DA(n) of after compression as in the above described conventional case.

Here, a case where the average values DA(n) of after compression are used as they are is shown in the above formula (5). However, for example, low-pass filter processing can be performed by applying a SINC filter to the average values DA(n) of after compression, and the formula (5) may be applied to the averaged values DA(n) of after compression which are processed as above.

In such case, the average values DA(n) of after compression to which low-pass filter processing are substituted in DA(n) of the above formula (5) and the DAave is to be the average value of average values DA(n) of after compression on which low-pass filter processing is performed.

Next, the correction data generation unit 75 of the radiographic image processing unit 70 generates pieces of correction data Ds (m, n) on the basis of the profile of correction data ds(n) of section area Sk obtained for each section are Sk.

Figure 19:
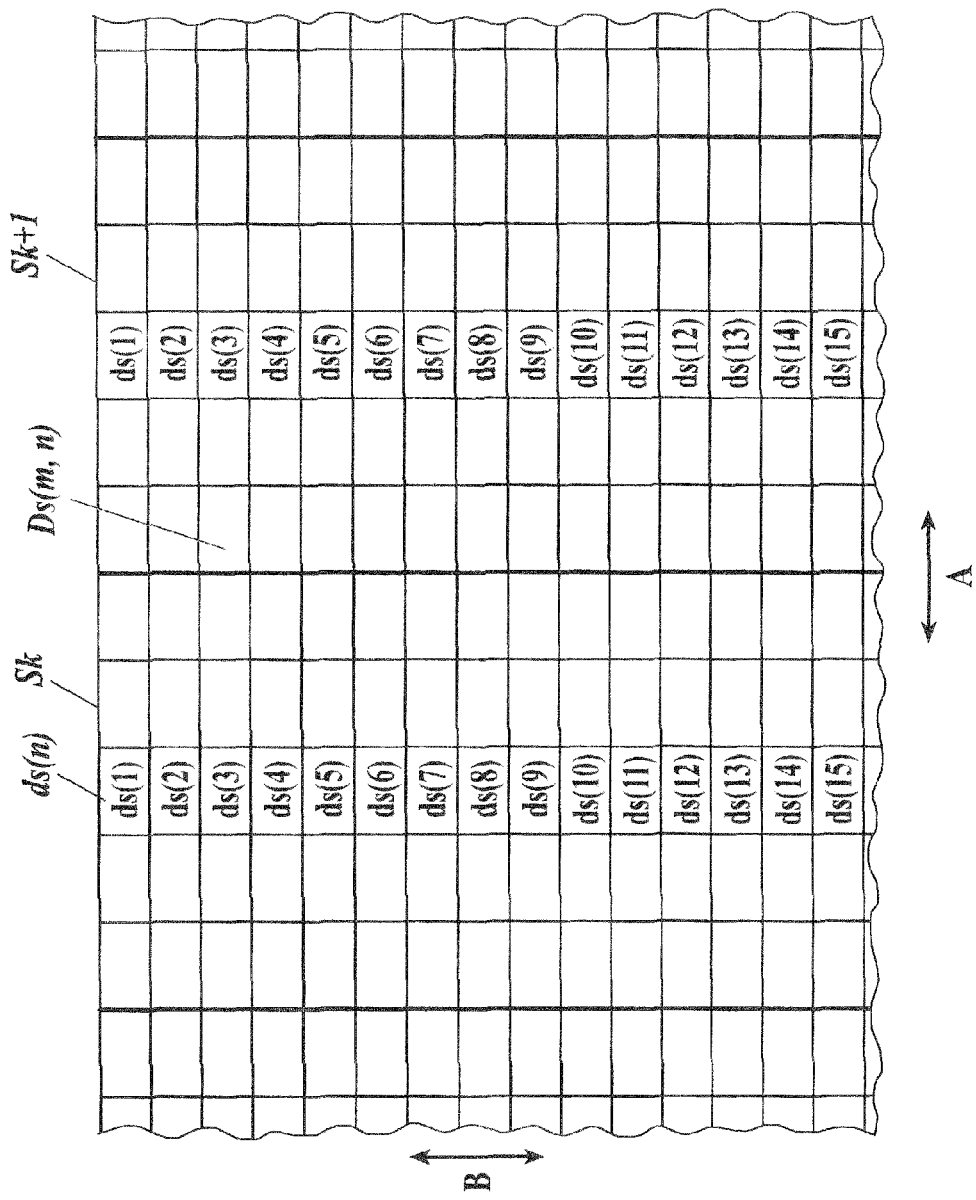
FIG. 19 This is a diagram for explaining a state where pieces of data on the profile of after filter processing are aligned along the extending direction of signal lines at the center in the scanning line direction in each section area.

In particular, as shown in FIG. 19, the correction data generation unit 75 aligns the correction data ds(n) of each section area Sk in the signal line direction B at the center position in the scanning line direction A in each section area Sk, for example, and generates pieces of correction data Ds (m, n) arranged in two dimensional manner by generating pieces of correction data Ds(m, n) at positions between the corresponding correction data ds(n) in adjacent section areas Sk by linear interpolation or the like.

In such way, in the processing performed by the units from dividing unit 71 to correction data generation unit 75 of the radiographic image processing apparatus 70, pieces of correction data Ds(m, n) consist only of streaky unevenness components (see FIG. 29) are extracted from the pieces of original image data Dori (m, n).

Then, as shown in FIG. 10, the radiographic image processing apparatus 70 generates pieces of image data D* in which streaky unevenness is removed by removing streaky unevenness from the pieces of original image data Dori (m, n) by subtracting it's corresponding piece of correction data Ds (m, n) from each piece of original image data Dori (m, n).

When the radiographic image processing apparatus 70 generates the pieces of image data D* in which streaky unevenness is removed, thereafter, the radiographic image processing apparatus 70 performs the well known image processing such as regularization processing, logarithmic conversion processing and tone processing on the generated pieces of image data D* and converts the generated pieces of image data D* into final image data (that is, image data for diagnosis) (step S4 in FIG. 9).

Here, when radiographic image capturing is carried out with the radiographic image capturing apparatus 1, there is a case where an image is captured with a grid being attached to the radiation entering surface R of the radiographic image capturing apparatus 1 (see FIG. 2, for example). In such case, unevenness (hereinafter, this is called grid moire to distinguish from the above mentioned streaky unevenness) appears in a radiographic image due to the grid. However, such grid moire appears in the image at long-period comparing to the above mentioned streaky unevenness, and therefore, the grid moire cannot be fully removed by the unevenness removing processing (step S3) or the grid moire cannot be removed.

Therefore, in such case, the radiographic image processing apparatus 70 performs a well known image processing for removing moire on the final image data generated from the pieces of image data D* and performs processing for removing the grid moire from the image data (step S5).

Then, the radiographic image processing apparatus 70 stores the final image data generated as described above in the storage unit 70b (step S6). Further, the radiographic image processing apparatus 70 records and outputs the radiographic image based on the final image data on an image recording medium such as a film by an imager or sends the radiographic image based on the final image data to a main computer of a hospital or a clinic to be stored.

As described above, according to the radiographic image processing apparatus 70 according to the embodiment, only the streaky unevenness components are extracted from the original image data Dori which is obtained by pre-processing being performed on image data D by the units which are the dividing unit 71, the average value calculation unit 72, the edge compression unit 73, the filter processing unit 74 and the correction data generation unit 75 performing their processing, and the correction data Ds consists only of streaky unevenness components is generated.

As described above, when radiographic image capturing is carried out with a FPD type radiographic image capturing apparatus, streaky unevenness (see FIG. 29) which extends in the extending direction of scanning lines 5, characteristic to FPD type radiographic image capturing apparatus, occurs in a radiographic image when a radiographic image is generated on the basis of pieces of original image data Dori on which only normal pre-processing such as gain/off-set correction processing, deficiency correction processing and the like are performed.

However, by calculating average values of pieces of original image data Dori aligned in the extending direction of same scanning lines 5 in each section area Sk by the average value calculation unit 72, the streaky unevenness components can be extracted without the streaky unevenness components cancelling each other out. Further, by applying a wiener filter as shown in the above mentioned formula (5), for example, by the filter processing unit 74, data in which streaky unevenness appears intensely can be extracted accurately.

Therefore, by performing the processing by the units which are the dividing unit 71 to the correction data generation unit 75, only the streaky unevenness components which extend in the extending direction of scanning lines 5 can be extracted accurately from the original image data Dori and the correction data Ds consists only of the streaky unevenness components can be generated.

Then, by subtracting it's corresponding correction data Ds from each piece of original image data Dori, the streaky unevenness superimposed on each piece of original image data Dori can be removed accurately and pieces of image data D* in which the streaky unevenness is removed can be generated accurately.

Therefore, by generating a radiographic image on the basis of the pieces of image data D* in which the streaky unevenness components are removed, the streaky unevenness will be removed from the radiographic image and the radiographic image without streaky unevenness can be generated.

Here, as described above, by calculating average values Da(n) of pieces of original image data Dori (m, n) in the scanning line direction A for each section area Sk by the average value calculation unit 72 of the radiographic image processing apparatus 70, noise components other than the streaky unevenness components are decreased by cancelling each other out and the average values Da(n) can be data in which the streaky unevenness components are the main noise components.

Therefore, by extending this, it can be considered that configuration may be such that average values Da(n) of pieces of original image data Dori (m, n) in the scanning line direction A are calculated with respect to the entire region Q without dividing the region Q into section areas Sk by sectioning the region Q in units of a predetermined number of pieces of original image data Dori at least in the scanning line direction A by the dividing unit 71 as shown in FIG. 12, the region Q being formed by having the pieces of original image data Dori (m, n) arranged in two dimensional manner.

However, when it is configured to calculate the average values Da(n) with respect to the entire region Q, a plurality of edge parts indicated by "a" and "b" in FIG. 14 appear in the profile of average values Da(n) and it will be difficult to appropriately compress the edge parts by the edge compression unit 73 as described above.

Moreover, when the predetermined number of pieces of original image data is small (that is, when the width of each section area Sk in the scanning line direction A is small, simply put), the extent of noise components other than the streaky unevenness components being decreased by cancelling each other out becomes small at the time of calculating the average values Da(n) of pieces of original image data Dori (m, n) in the scanning line direction A by the average value calculation unit 72 as described above, and noise components other than the streaky unevenness components will be included in the average values Da(n) in large quantity.

Therefore, the streaky unevenness components cannot be extracted accurately even when the processing are performed by the units which are the edge compression unit 73 and thereafter on such average values Da(n), and the correction data Ds consists only of streaky unevenness components (see FIG. 29) cannot be formed accurately. Thus, the predetermined number of pieces of original image data of when sectioning the region Q in units of the predetermined number of pieces of original image data Dori in the scanning line direction A by the dividing unit 71 is set to an arbitrary number.

At that time, when the predetermined number is set to a number obtained by dividing the total number of pieces of original image data Dori in the scanning line direction A in the region Q by a natural number, the number of pieces of original image data Dori which are target for averaging when calculating average values Da(n) for each section area Sk by the average value calculation unit 72 will be the same number and the processing configuration of arithmetic processing is to be simple. Further, the calculated average values Da(n) can be handled uniformly.

On the other hand, when the predetermine number of pieces of original image data applied when dividing the region Q is set as a large number as described above, a plurality of edge parts appear in the profile of average values Da(n) and it is difficult to appropriately compress the edge parts by the edge compression unit 73. However, if the edge parts cannot be compressed and removed accurately, the edge parts remain in the correction data Ds. Further, because the edge parts in the correction data Ds is to be subtracted from the edge parts in the original image data Dori when the correction data Ds is subtracted from the original image data Dori, the pieces of image data D* in which the streaky unevenness is removed become data in which edge parts are blurred.

When a radiographic image is generated on the basis of such pieces of image data D*, the radiographic image is to be an image in which the border between the part where internal organ, bone or the like in a body, for example, is captured and other parts becomes blurred and image quality is degraded. In such way, edge parts need to be appropriately detected and accurately compressed by the edge compression unit 73.

In view of the above, the region Q is divided in small sections by the dividing unit 71, that is, the above mentioned predetermined number of pieces of original image is set to a small number so that there will be a large number of section areas Sk in which edge part is not included and so that the edge parts can be appropriately detected by the edge compression unit 73 even when the edge parts are included in the section areas Sk, and processing of the edge compression unit 73 and the filter processing unit 74 are performed.

Figure 20:
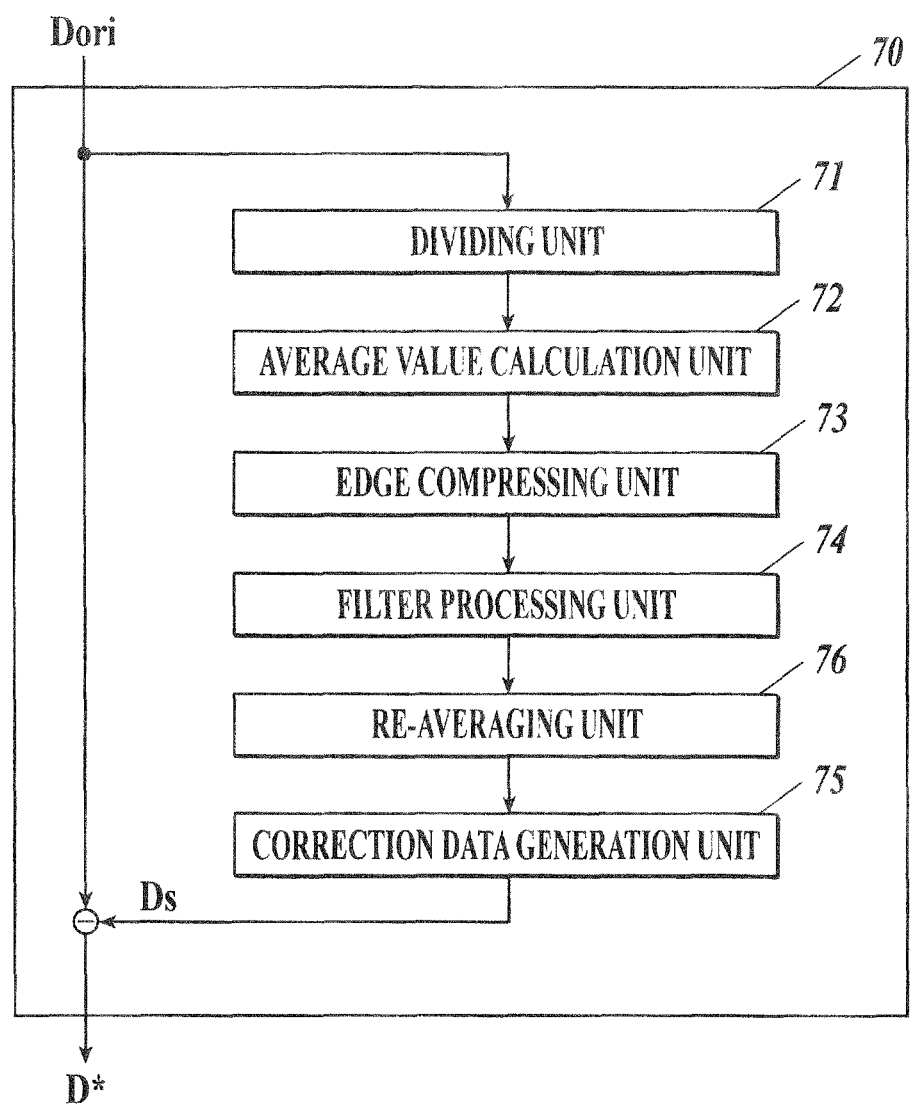
FIG. 20 This is a block diagram showing a functional configuration of the radiographic image processing apparatus when a re-averaging unit is provided.

Further, as shown in FIG. 20, configuration may be such that a re-averaging unit 76 is provided between the filter processing unit 74 and the correction data generation unit 75 and average values ds(n)ave of correction data ds(n) in the scanning line direction A for each section area Sk are calculated with respect to each of the predetermined number of section areas Sk which are adjacent to each other by the re-averaging unit 76 after performing edge compression processing and filter processing on the scanning line direction A profile of average values Da(n) of pieces of original image data Dori in each of the section areas Sk which are divided in small sections as described above.

On the basis of the pieces of average values ds(n)ave calculated by the re-averaging unit 76, the correction data generation unit 75 aligns the average values ds(n)ave in the signal line direction B at the center position in each of the section areas Sk in the scanning line direction A, the plurality of number of section areas Sk being adjacent to each other as described above, as described in FIG. 19 and reconstructs the pieces of data in other positions in the region Q by linear interpolation or the like so as to generate the correction data Ds aligned in two dimensional manner.

By having such configuration, there will be a large number of section areas Sk in which edge parts are not included among the section areas Sk generated by the region Q being sectioned in small sections and the number of edge parts included in a section area Sk becomes small and the edge parts appear clearly in the section areas Sk in which edge parts are included. Therefore, the edge parts can be accurately detected and compressed by the edge compression unit 73.

Moreover, by calculating the average values ds(n)ave of the correction data ds(n) in the scanning line direction A for each section area Sk with respect to the predetermined number of section areas sk which are adjacent to each other by the re-averaging unit 76 after the filter processing is performed on the section areas Sk which do not include edge parts and the scanning line direction A profiles of average values DA(n) of the pieces of original image data Dori in the section areas Sk in which the edge parts are accurately compressed, noise components other than the streaky unevenness are decreased by cancelling each other out as described above. Therefore, the calculated average values ds(n)ave becomes data in which the streaky unevenness components are the main noise component.

When the edge parts in the scanning line direction A profile of average values Da(n) of pieces of original image data Dori of each section area Sk are to be compressed by the edge compression unit 73 as described above, the streaky unevenness components at the edge parts disappear by compressing the average value Da(n) of those parts even if streaky unevenness components exist at the edge parts.

That is, even if streaky unevenness information remains in the average values Da(n) of before compression, the information disappears in the average values DA(n) of after compression. Therefore, in view of extracting streaky unevenness components, it cannot be said that the values of average values DA(n) at the edge parts are necessarily reliable data.

Therefore, for example, if the edge compression unit 73 detects edge parts in the profile of each section area Sk, their positions, that is, n=a and n=b in the section area Sk shown in FIG. 14, for example, are stored in the storage unit 70b for each section area Sk. Further, after filter processing is performed by the filter processing unit 74, a profile of average values ds(n) all of correction data ds(n) in the scanning direction A for each section area Sk is generated with respect to the entire section areas Sk on the basis of the profile of correction data ds(n) of each section area Sk obtained for each of the section areas Sk.

Further, with respect to the correction data ds(n) of each section area Sk at the edge parts in each section are Sk, the streaky unevenness components at the edge parts of each section area Sk disappeared in the edge compression processing performed by the edge compression unit 73 can be reconstructed by discarding the data ds(n) calculated to each section area Sk and replacing with the average values ds(n) all of the entire section areas Sk.

Second Embodiment

As described above, streaky unevenness superimposed on image data D and original image data Dori occurs due to voltage noise generated in the power supply 15a (see FIG. 7) of the scanning drive unit 15, the bias power supply 14 and the like being transmitted to the radiation detection elements 7 and the TFTs 8 via the scanning lines 5 and the bias lines 9.

Further, because the timing when ON voltage is applied to each of the lines L1 to Lx of scanning lines 5 is different at the time of read-out processing of image data D, although the same noise is to be superimposed on the radiation detection elements 7 connected to the same scanning line 5, size of the noise is to be a different value in a different scanning line 5. Therefore, as shown in FIG. 29 by being enlarged, streaky unevenness which extends in the scanning line direction A appears in the radiographic image p, that is, pieces of image data D.

In the above described first embodiment, because at least the scanning lines 5 are arranged in the entire area (that is, in the entire region from the left side to the right side in case of FIG. 5) of the detection unit P as shown in FIG. 5, pieces of original image data Dori on which gain/off-set correction processing is performed are arranged in two dimensional manner so as to correspond respectively to the plurality of radiation detection elements 7 which are arranged in two dimensional manner on the detection unit P, and processing is performed by the dividing unit 71 and thereafter.

Figure 21:
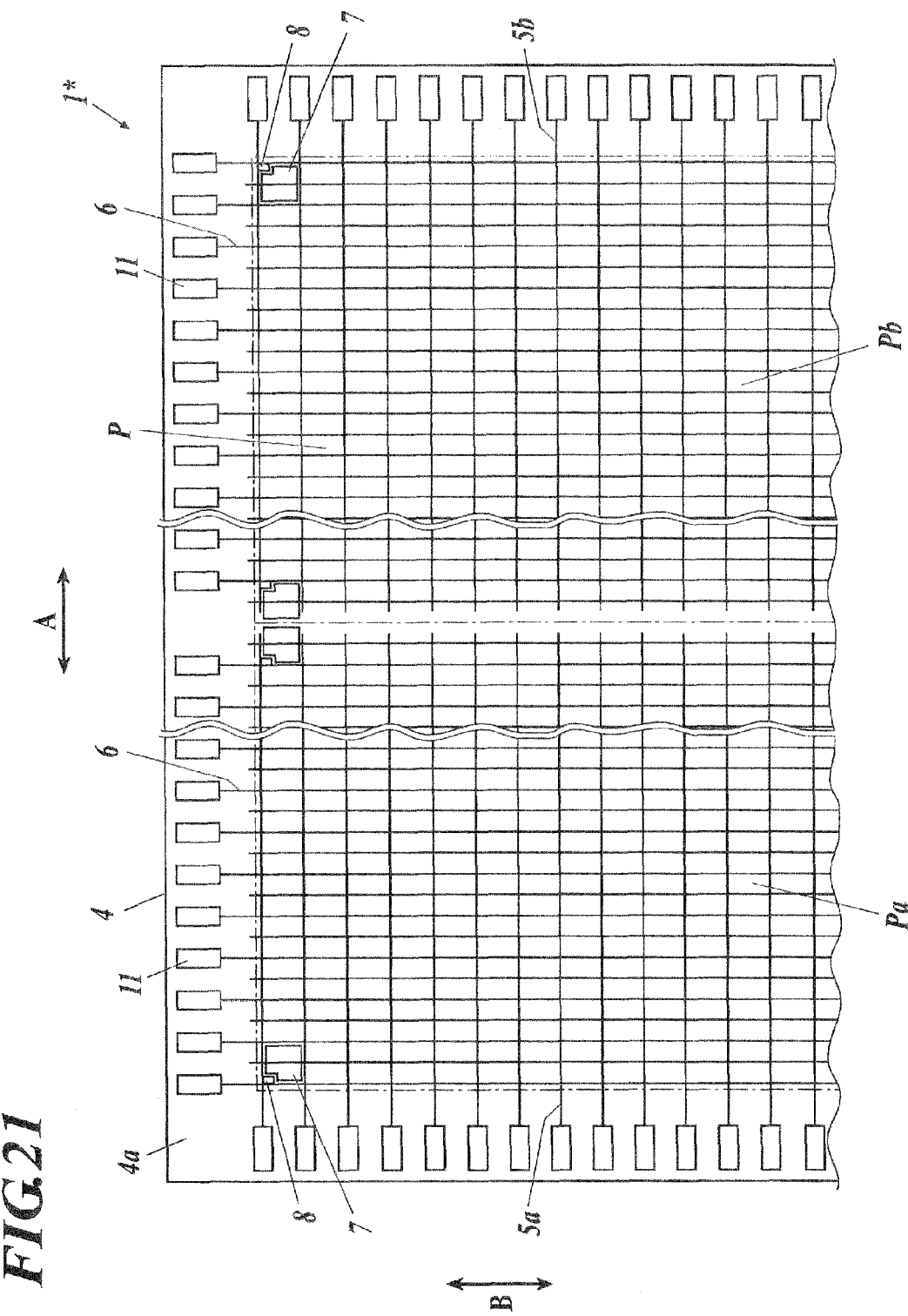
FIG. 21 This is a plane view showing a configuration of a substrate of the radiographic image capturing apparatus which is structured by each scanning line being divided.

However, FPD type radiographic image capturing apparatus includes a radiographic image capturing apparatus 1* having configuration where at least the scanning lined 5 are divided into scanning lines 5a and scanning lines 5b in the scanning line direction A on the detection unit P as shown in FIG. 21, for example.

In such radiographic image capturing apparatus 1*, there is a case where the noises transmit to radiation detection elements 7 via the scanning lines 5a and 5b differs between the regions Pa and Pb in the detection unit P in each of which the divided scanning lines 5a and 5b exist, respectively. Further, there is a case where the read-out processing and the like is not necessarily performed at the same timing in the regions Pa and Pb.

Figure 22:
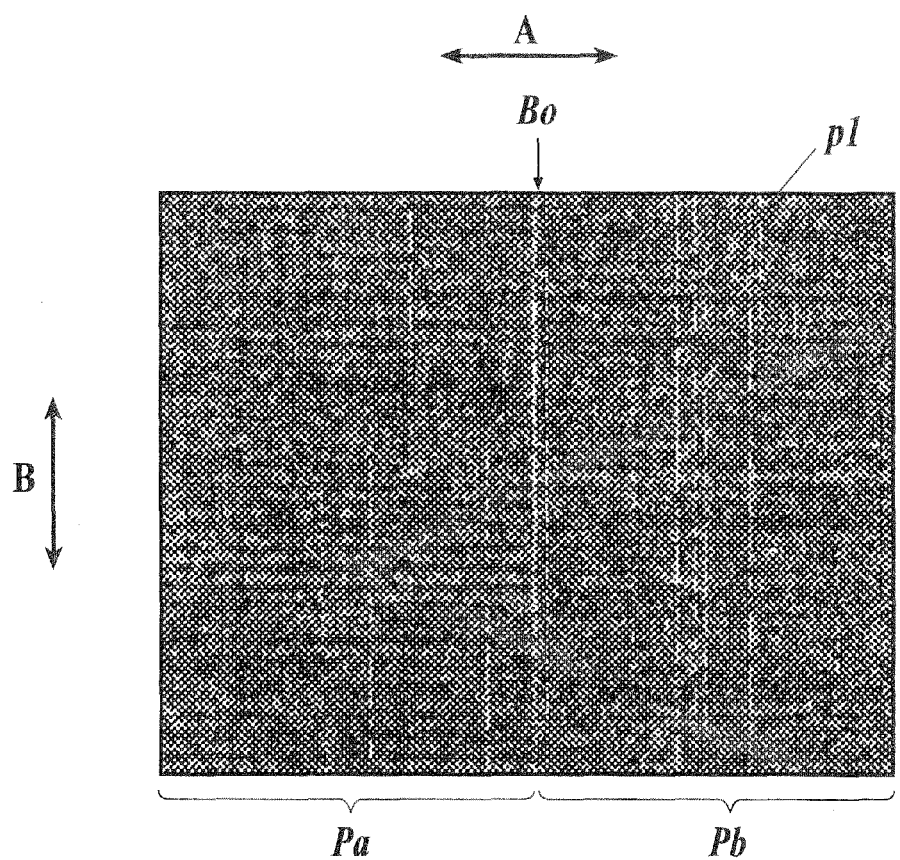
FIG. 22 This is a photograph which is captured with the radiographic image capturing apparatus shown in FIG. 21 which is an enlarged photograph of a radiographic image generated on the basis of original image data on which only pre-processing is performed.

In such cases, if a radiographic image p1 is to be generated on the basis of the pieces of original image data Dori generated by a pre-processing being performed in the pieces of image data captured with the radiographic image capturing apparatus 1*, streaky unevenness that extend in the scanning line direction A appears differently in regions corresponding to the regions Pa and Pb of the detection unit P as shown in FIG. 22 by being enlarged.

Figure 23:
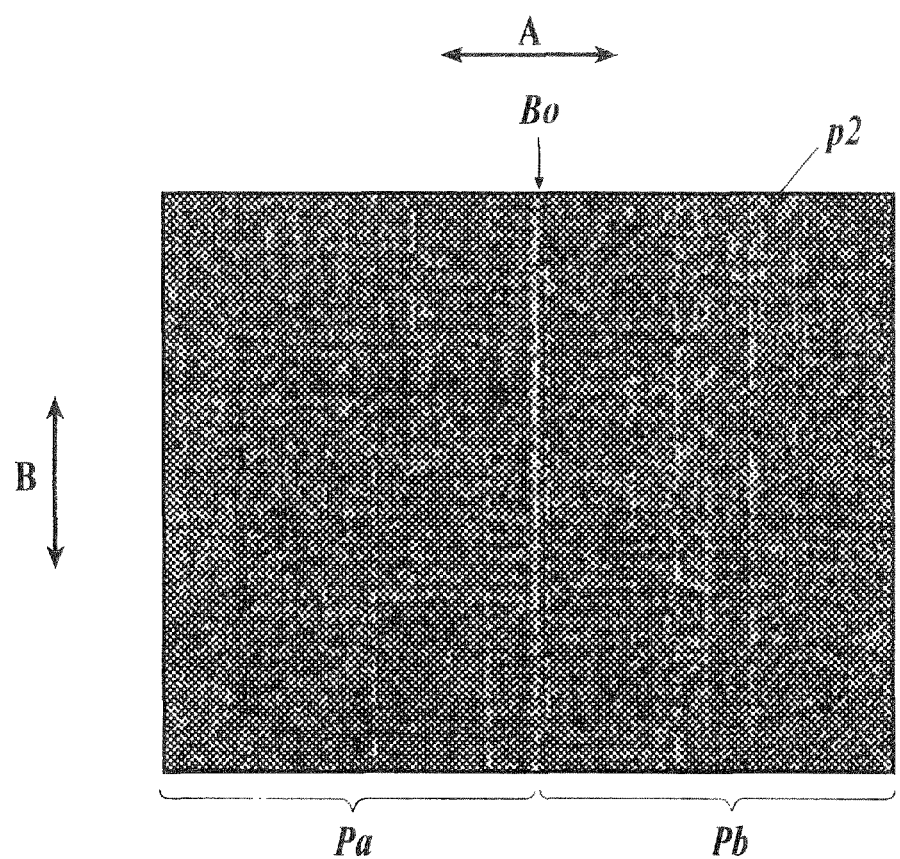
FIG. 23 This is a photograph which is captured with the radiographic image capturing apparatus shown in FIG. 21 which is an enlarged photograph of a radiographic image generated on the basis of original image data processed without distinguishing each region of the detection unit.
Figure 24:
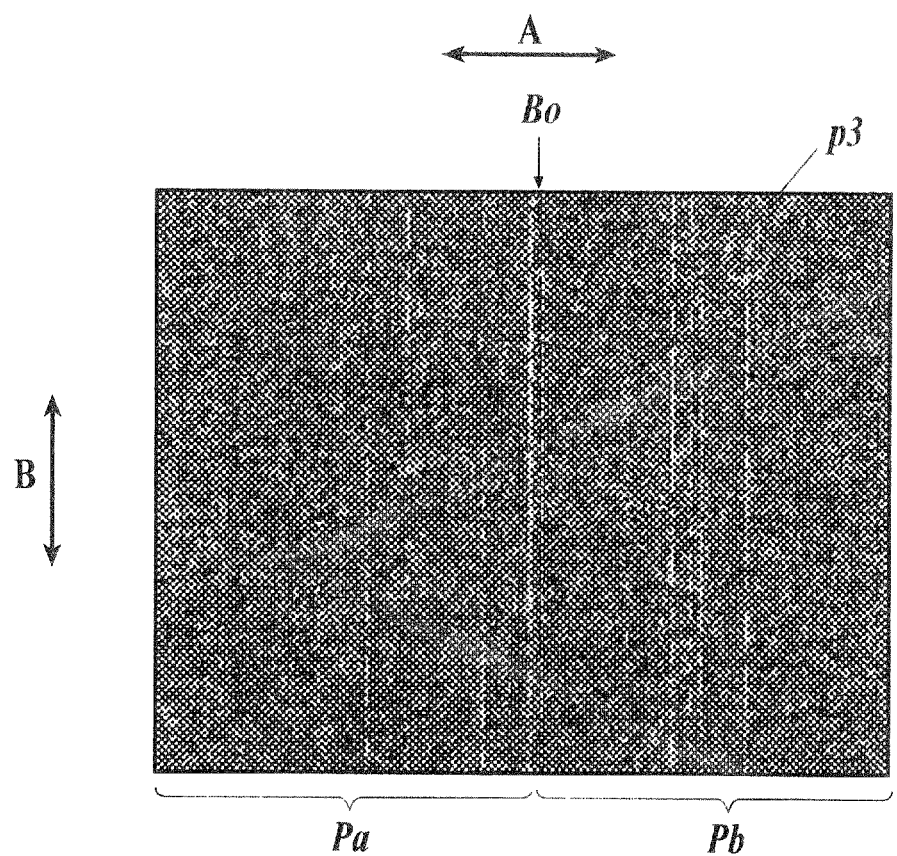
FIG. 24 This is a photograph which is captured with the radiographic image capturing apparatus shown in FIG. 21 which is an enlarged photograph of a radiographic image generated on the basis of original image data processed region by region in the detection unit.

Here, in FIG. 22 and the after mentioned FIGS. 23 and 24, streaky unevenness that extends in the signal line direction B in a radiographic image is derived from the read out characteristic of each read-out circuit 17 corrected to each signal line 6 and this is different from the streaky unevenness that extends in the scanning line direction in the present invention. With respect to such streaky unevenness that extends in the signal line direction B, different processing to removing the unevenness is properly performed.

Further, similarly to the first embodiment, when processing is performed by the units which are the dividing unit 71 and thereafter by arranging the pieces of original image data Dori in two dimensional manner so as to correspond respectively with the plurality of radiation detection elements 7 which are arranged in two dimensional manner in the entire region of the detection unit P, influence such as streaky unevenness appearing differently in the regions Pa and Pb in the radiographic image p2, specifically, at near the border Bo of the regions Pa and Pb cannot be avoided completely as shown in FIG. 23, and there may be a phenomenon where streaky unevenness remain not being able to be removed completely.

In view of the above, it is preferred that the image processing described in the first embodiment is performed on the pieces of image data D captured with the radiographic image capturing apparatus 1* in which at least the scanning lines 5 are divided in the scanning line direction A on the detection unit P as described above individually with respect to the pieces of image data D obtained in the region Pa of the detection unit P and with respect to the pieces of image data D obtained in the region Pb of the detection unit P, the divided scanning lines 5a and 5b existing respectively in the regions Pa and Pb.

By having such configuration, different correction data Ds are extracted and generated from the pieces of original image data Dori based on the pieces of image data obtained in the regions Pa and Pb of the detection unit P and the different correction data Ds are subtracted from the pieces of original image data Dori individually.

Therefore, with respect to the pieces of original image data Dori based on the pieces of image data D obtained in the region Pa of the detection unit P, the correction data Ds generated by being extracted therefrom is subtracted and with respect to the pieces of original image data Dori based on the pieces of image data D obtained in the region Pb of the detection unit P, the correction data Ds generated by being extracted therefrom is subtracted. Thus, of image data D* in which streaky unevenness is removed can be generated accurately in each of the regions Pa and Pb of the detection unit P.

Therefore, as shown in FIG. 24 by being enlarged, streaky unevenness can be removed accurately in the radiographic image p3 which is generated on the basis of the pieces of image data D* accurately generated as described above, and further, streaky unevenness will not be remained near the border Bo of the regions Pa and Pb.

Third Embodiment

In the first and the second embodiments, descriptions are given for the case where with respect to the pieces of image data D read out in the radiographic image capturing apparatus 1, pieces of original image data Dori are generated by performing pre-processing such as gain/off-set correction processing, correction data ds is generated by the units from the dividing unit 71 to the correction data generation processing 75 performing their processing on the pieces of original image data Dori and pieces of image data D* in which streaky unevenness is removed are generated by subtracting it's corresponding correction data Ds from each piece of original image data Dori.

On the other hand, because reading out is performed by the similar processing as in the radiographic image capturing except for emitting radiation to the radiographic image capturing apparatus 1 in the dark reading processing for obtaining off-set correction values to be subtracted from the pieces of image data D in the gain/off-set correction processing (step S1 of FIG. 9), streaky unevenness that extends in the scanning line direction A similarly in the image data D is superimposed on the off-set correction values O.

Further, because the dark reading processing cannot be performed at the same time as radiographic image capturing and is performed before or after radiographic image capturing, the streaky unevenness which is superimposed on the pieces of off-set correction values O which are read out by the dark reading processing and the streaky unevenness which is superimposed on the pieces of image data D which are read out by the read-out processing in radiographic image capturing are completely different.

However, when each off-set correction value O is subtracted from it's corresponding piece of image data D according to the formula (1) in the gain/off-set correction processing, streaky unevenness generated by the streaky unevenness superimposed on the off-set correction value O from the streaky unevenness superimposed on the piece of image data D is superimposed on the value D−O obtained by the above subtraction.

Therefore, configuration may be such that pieces of original image data Dori are generated by multiplying the value D−O on which the streaky unevenness is superimposed by a gain correction value G and to perform image processing on the generated pieces of original image data Dori. This corresponding to the case described in the first embodiment and the second embodiment.

However, when off-set correction values O on which other streaky unevenness is superimposed are subtracted respectively from pieces of image data D on which streaky unevenness is superimposed, the streaky unevenness superimposed on the values D−O obtained by the above subtraction is to be multiplied by square root of 2 in it's size, that is, to be about 1.4 times the size. Further, when the streaky unevenness to be superimposed on the image data D is relatively large to start with, there is a case where the streaky unevenness to be superimposed on the values D−O obtained by the above subtraction is to be abnormally large and the streaky unevenness cannot be removed accurately from the original image data Dori.

In view of the above, processing similar to that performed on the pieces of original image data Dori shown in the first and the second embodiments is performed on the off-set correction values O before subtracting the off-set correction values O from the pieces of image data D, respectively, according to the formula (1) in the gain/off-set correction processing (step S1 in FIG. 9) and off-set correction values O in which streaky unevenness is removed is generated in advance.

Further, configuration may be such that the off-set correction values O in which the streaky unevenness is removed are subtracted from the pieces of image data D on which streaky unevenness is superimposed, respectively, in the gain/off-set correction processing (step S1 in FIG. 9).

By having such configuration, the streaky unevenness superimposed on the original image data Dori do not become abnormally large and processing can be performed while maintaining the condition of streaky unevenness superimposed on the original image data D, and further, streaky unevenness can be removed accurately from the pieces of original image data Dori.

Moreover, as described above, the off-set correction values O are obtained by the dark reading processing performed in a state where radiation is not emitted onto the radiographic image capturing apparatus 1. Therefore, differently from the case of pieces of original image data Dori, information on an internal organ, a bone or the like in a human body is not included in the off-set correction values O and the edge parts as mentioned above do not exist.

Figure 7:
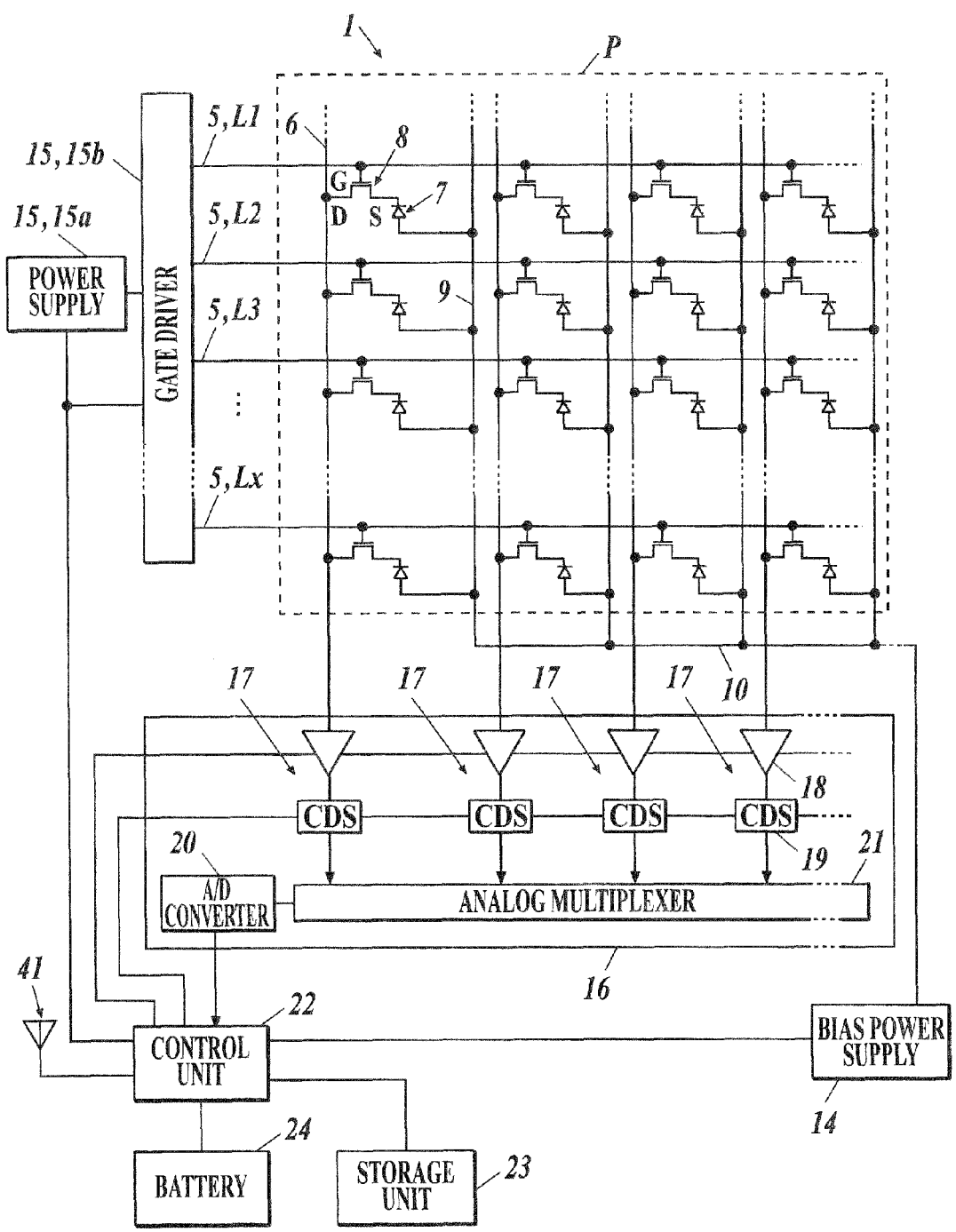
FIG. 7 This is a block diagram showing an equivalent circuit of the radiographic image capturing apparatus.
Figure 8:
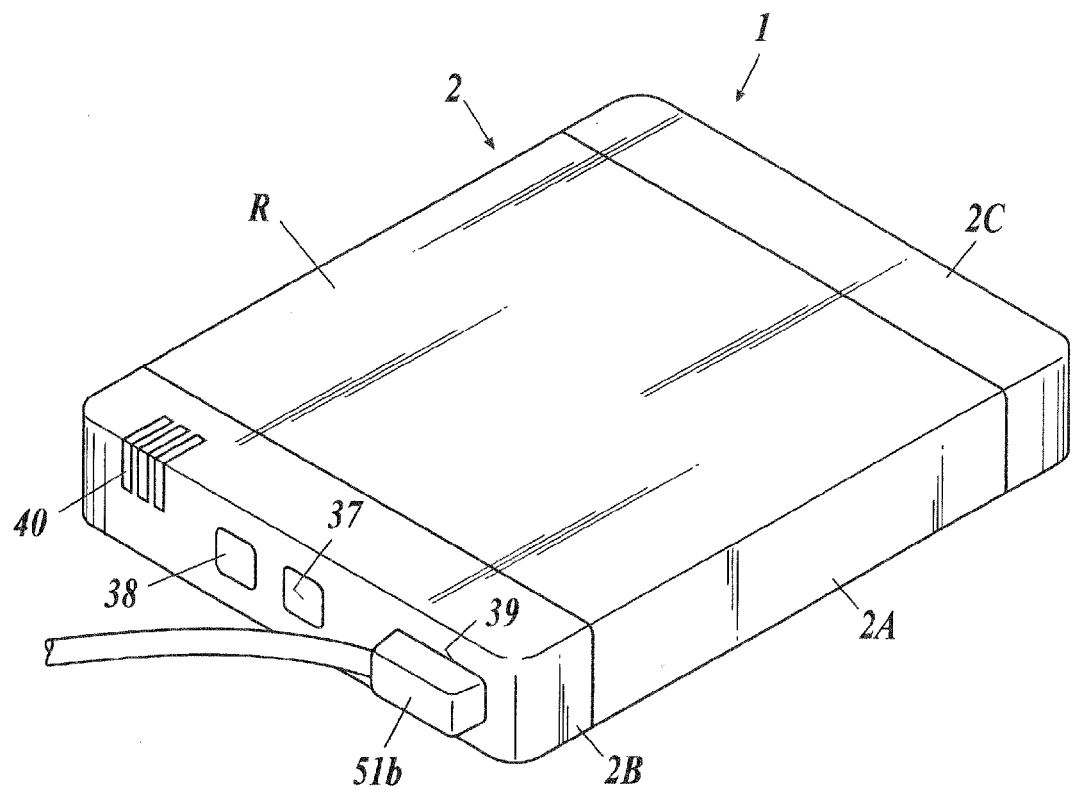
FIG. 8 This is an outer schematic view showing a state where a connector of the radiographic image capturing apparatus and a connector of a bucky are connected.

Therefore, in the processing performed on the off-set correction values O, configuration may be such that processing of the unit which are the average value calculation unit 72 to the correction data generation unit 75 is performed on the entire region Q with out dividing the region Q by the dividing unit 71 where the off-set correction values O are arranged two dimensionally in the region Q so as to correspond respectively to the plurality of radiation detection elements 7 which are arranged two dimensionally on the detection unit P (see FIGS. 5 and 7).

On the other hand, in order to strictly remove the streaky unevenness from the off-set correction values O, configuration may be as described bellow.

That is, a plurality of off-set correction values O for each radiation detection element 7 are obtained by performing the dark reading processing for a plurality of times in the radiographic image capturing apparatus 1 in advance, and an off-set correction value O of each radiation detection element 7 is calculated as an average value of the above off-set correction values O and stores the calculated off-set correction value O in the storage unit 70b of the radiographic image processing apparatus 70.

Hereinafter, the off-set correction value O which is obtained in advance for each radiation detection element 7 is called the reference off-set correction value Oc to distinguish from the off-set correction value O obtained in every radiographic image capturing.

Further, because the dark reading processing for obtaining the reference off-set correction value Oc is performed for a plurality of times and the condition of streaky unevenness to be superimposed on the off-set correction value O differs in each dark reading processing, that is, because the line L of scanning lines 5 in which streaky unevenness appears intensely and the line L of scanning line 5 in which streaky unevenness appears weakly differ in each dark reading processing, the streaky unevenness superimposed on the off-set correction values O cancel each other out by averaging the off-set correction values O obtained by the plurality of times of dark reading processing. Therefore, the reference off-set correction value Oc will not have streaky unevenness superimposed thereon.

Figure 25:
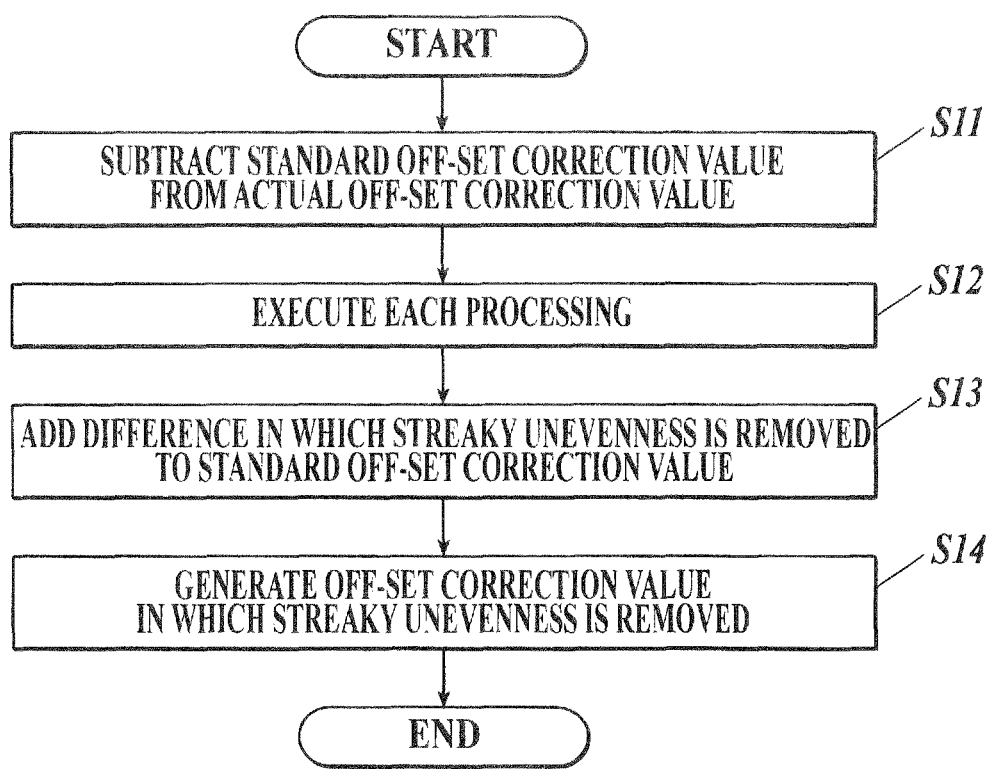
FIG. 25 This is a flowchart showing a procedure of processing for even more strictly removing streaky unevenness from off-set correction values.
Figure 26:
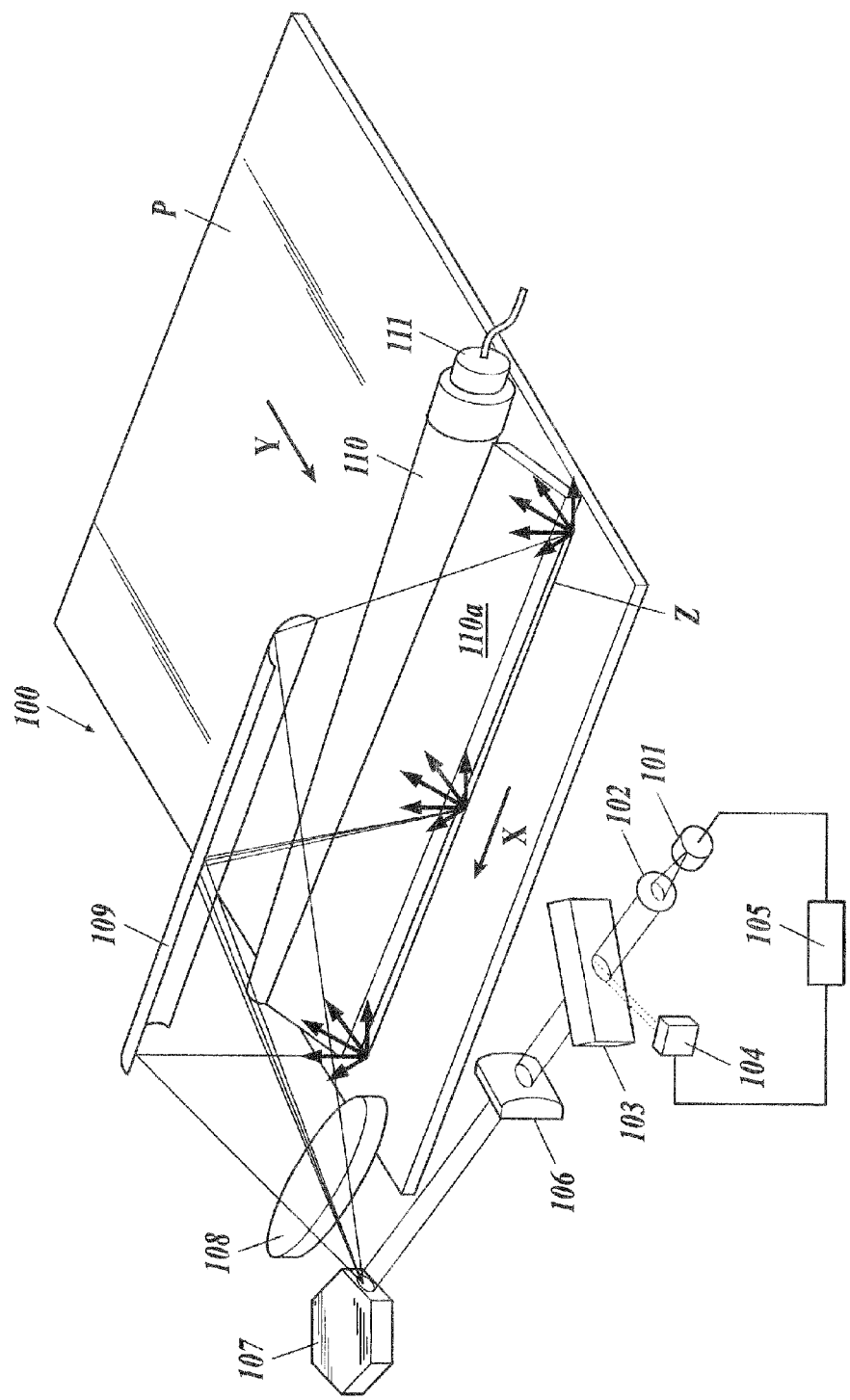
FIG. 26 This is a diagram showing a configuration of a radiographic image reading apparatus.
Figure 27:
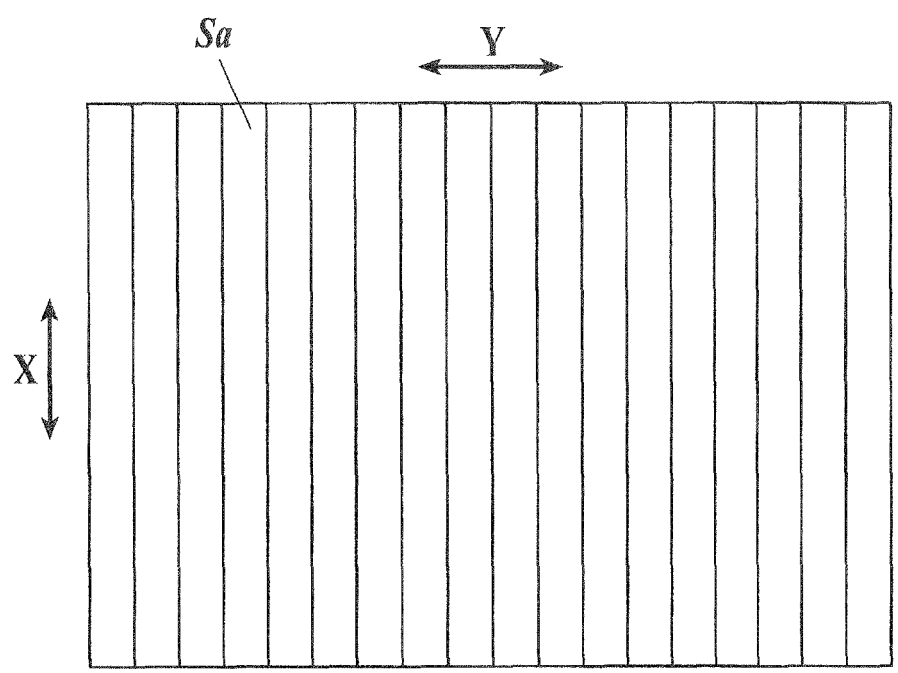
FIG. 27 This is a diagram for explaining that image data arranged in two dimensional manner is divided into strip-shaped areas.

In the radiographic image processing apparatus 70, streaky unevenness is removed from the actual off-set correction values O obtained by the dark reading processing which is performed before or after each radiographic image capturing to generate off-set correction values in which streaky unevenness is removed according to the flowchart shown in FIG. 25 in a state having the reference off-set correction value Oc.

First, the radiographic image processing apparatus 70 subtracts the reference off-set correction value Oc from the actual off-set correction valued O obtained in each dark reading processing with respect to each radiation detection element 7 and calculates differences $\Delta O$ for each radiation detection element 7 (step S11). As described above, streaky unevenness is not superimposed on the reference off-set correction value Oc, the differences $\Delta O$ are to be in a state where the streaky unevenness superimposed on the actual off-set correction values O is superimposed.

Further, the radiographic image processing apparatus 70 performs the above mentioned processing of the units from the dividing unit 71 to the correction data generation unit 75 on the calculated differences $\Delta O$ (step S12). Here, in such case, information on an internal organ, a bone or the like in a human body is not included in the differences $\Delta O$ and there is no need to perform the dividing processing of the dividing unit 71 because there is no edge parts as described above.

Then, when correction data $\Delta Os$ of the differences $\Delta O$ is generated by the correction data generation unit 75, it's corresponding correction data $\Delta Os$ is subtracted from the original differences ΔO and differences ΔO* in which streaky unevenness is removed are generated.

Next, the radiographic image processing apparatus 70 adds the generated differences ΔO* in which streaky unevenness is removed to the off-set correction values Oc which are references, respectively (step S13). As described above, streaky unevenness is not superimposed on the off-set correction values Oc which are references and further because streaky unevenness is also removed from the differences ΔO*, streaky unevenness is removed from the sum values where the off-set correction values Oc which are references are added respectively with the differences ΔO*.

Therefore, the radiographic image processing apparatus 70 stores the sum values where the off-set correction values Oc which are references are added respectively with the differences ΔO* in which streaky unevenness is removed in the storage unit 70b as off-set correction values O* in which streaky unevenness is removed. In such way, the radiographic image processing apparatus 70 generates the off-set correction values O* in which streaky unevenness is removed from the actual off-set correction values O (step S14).

Here, it is needless to say that the off-set correction values O* in which streaky unevenness is removed generated as described above are substituted in the formula (1) to generate the original image data Dori, and the processing of the units from the dividing unit 71 to the correction data generation unit 75 is performed again on the original image data Dori to subtract the generated correction data Ds from the original image data Dori and pieces of image data D* in which streaky unevenness is removed are generated.

By having such configuration, because the streaky unevenness is accurately removed from the off-set correction values O, the processing for removing the streaky unevenness can be performed appropriately on the original image data Dori which is obtained by subtracting the generated off-set correction values O* in which streaky unevenness is removed from the image data D, and further, pieces of image data D* in which streaky unevenness is removed can be generated accurately.

INDUSTRIAL APPLICABILITY

The present invention can be applied to the field of radiographic image capturing (especially in medical fields).

DESCRIPTION OF MARKS 1 radiographic image capturing apparatus
L1 to Lx scanning line
6 signal line
7 radiation detection element
70 radiographic image processing apparatus
71 dividing unit
72 average value calculating unit
73 edge compression unit
74 filter processing unit
75 correction data generation unit
76 re-averaging unit
A scanning line direction (extending direction of scanning line)
B signal line direction (extending direction of signal line)
D image data
D* image data in which noise is removed
DAave average value of average values in a profile in which differences are compressed of each section area
Da(n) average calue
Da(n)−Da(n−1) difference
Dori original image data (image data)
Ds, Ds (m, n) correction data
ds(n) correction data of each section area (pieces of data in a profile on which adaptive filter is applied)
ds(n)ave average value of correction data of each section area
O off-set correction value
O* off-set correction value in which noise is removed
Oc off-set correction value which is reference
P detection unit
Pa, Pb each region in detection unit
Q region
r section
Sk each section area
ΔDath threshold
ΔO difference
ΔO* difference in noise is removed
ΔOs correction data
$\sigma^2(n)$ variance of average values in a profile in which differences are compressed
$\sigma v^2$ value of variance which is pre-set

The invention claimed is:

1. A radiographic image processing apparatus which performs image processing on pieces of image data of radiation detection elements captured by a radiographic image capturing apparatus, wherein the radiographic image capturing apparatus comprises a detection unit in which radiology detection elements are arranged in a two dimensional manner, the radiology detection elements being provided respectively in sections which are sectioned by a plurality of scanning lines and a plurality of signal lines arranged so as to intersect each other, the radiographic image processing apparatus comprising:

a dividing unit which divides a region in section areas by sectioning the region, in which the pieces of image data are arranged in a two dimensional manner, in units of a predetermined number of pieces of image data at least in an extending direction of the scanning line on the detection unit when the pieces of image data are arranged in a two dimensional manner so as to correspond respectively with the plurality of radiation detection elements arranged in a two dimensional manner;

an average value calculation unit which performs a calculation of an average value of the pieces of image data aligned in the extending direction of a same scanning line among the pieces of image data in a section area for each of the scanning lines for each of the section areas;

an edge compression unit which generates a profile in which a difference in average values of the pieces of image data which occurs at a border of a captured subject and a surrounding thereof is compressed for each of the section areas with respect to a signal line extending direction profile of the average values of the pieces of image data of individual scanning lines calculated for each of the section areas;

a filter processing unit which performs processing to apply an adaptive filter to the profile in which the differences are compressed for each of the section areas; and a correction data generation unit which generates pieces of correction data arranged in a two dimensional manner by reconstructing pieces of data at other positions in the region based on pieces of data in the profiles to which the adaptive filter is applied, wherein pieces of image data in which noises are removed are generated respectively for the radiation detection elements by subtracting the pieces of correction data of corresponding positions from the pieces of image data arranged in a two dimensional manner, respectively.

2. The radiographic image processing apparatus of claim 1, wherein the filter processing unit applies a wiener filter as the adaptive filter to the profile in which the differences are compressed.

3. The radiographic image processing apparatus of claim 2, wherein the filter processing unit applies the wiener filter to the profile in which the differences are compressed in a form expressed in a formula (1) and sets a value obtained by subtracting a value Df(n) which is calculated from the average values in the profile in which the differences are compressed as data in the profile to which the adaptive filter is applied, the formula (1) being $$Df(n) = DAave + \frac{\sigma^2(n) - \sigma^2 v}{\sigma^2(n)}(DA(n) - DAave) \qquad \text{[formula 1]}$$

where Df(n) represents a value of data after filter processing, DAave represents an average value of the average values in the profile where the difference is compressed obtained for each of the section areas, $\sigma v^2$ represents a value of variance which is pre-set, $\sigma^2(n)$ represents a variance of the average values in the profile in which the differences are compressed.

4. The radiographic image processing apparatus of claim 2, wherein the filter processing unit performs low-pass filter processing on the average values in the profile in which the differences are compressed and applies the wiener filter.

5. The radiographic image processing apparatus of claim 1, wherein the predetermined number which is applied when sectioning the region in units of the predetermined number of pieces of image data at least in the extending direction of the scanning lines on the detection unit by the dividing unit is set to a number obtained by dividing a total number of the pieces of image data in the extending direction of the scanning lines in the region by a natural number.

6. The radiographic image processing apparatus of claim 1, further comprising a re-averaging unit which performs calculation of an average value of the pieces of data in the extending direction of a same scanning line for each of the scanning lines among the pieces of data in the profile to which the adaptive filter is applied by the filter processing unit, with respect to each of the predetermined number of section areas which are adjacent to each other, wherein the correction data generation unit generates pieces of correction data arranged in a two dimensional manner by reconstructing pieces of data in other positions in the region based on the average values of the pieces of data which the re-averaging unit calculated.

7. The radiographic image processing apparatus of claim 1, wherein, with respect to the pieces of image data captured with the radiographic image capturing apparatus in which at least the plurality of scanning lines are divided in the extending direction of the scanning lines on the detection unit, each of processing performed by the dividing unit to processing performed by the correction data generation unit is performed individually to the pieces of image data obtained in each of regions in the detection unit where the plurality of scanning lines are divided and the pieces of correction data at corresponding positions are individually subtracted from the pieces of image data which are individually arranged two-dimensionally to generate the pieces of image data in which a noise is removed.

8. The radiographic image processing apparatus of claim 1, wherein, with respect to off-set correction values of the radiation detection elements obtained by the radiographic image capturing apparatus, processing of units from the dividing unit to the correction data generated unit is performed, the correction data of a corresponding position is subtracted from each of the pieces of off-set correction values arranged in a two dimensional manner to generate off-set correction values in which the noise is removed and the off-set correction values in which the noise is removed are subtracted respectively from the pieces of image data.

9. The radiographic image processing apparatus of claim 1, wherein:

off-set correction values which are references are set in advance respectively for the radiation detection elements in the radiographic image capturing apparatus, processing of units from the dividing unit to the correction data generation unit is performed on differences obtained by subtracting the off-set correction values which are references from off-set correction values obtained by the radiographic image capturing apparatus, respectively, differences in which a noise is removed are generated by subtracting the correction data at corresponding positions from the differences arranged in a two dimensional manner, respectively, off-set correction values in which a noise is removed for the radiation detection elements of the radiographic image capturing apparatus are generated by adding the differences in which the noise is removed to the off-set correction values which are references, respectively, and the off-set correction values in which the noise is removed are subtracted from the pieces of image data, respectively.

* * * * *